United States Patent
Aoki

(10) Patent No.: US 10,310,242 B2
(45) Date of Patent: Jun. 4, 2019

(54) OBSERVATION APPARATUS, METHOD FOR CONTROLLING OBSERVATION APPARATUS, AND NON-TRANSITORY COMPUTER READABLE STORAGE MEDIUM STORING CONTROL PROGRAM FOR OBSERVATION APPARATUS

(71) Applicant: Olympus Corporation, Tokyo (JP)

(72) Inventor: Takato Aoki, Hino (JP)

(73) Assignee: Olympus Corporation, Tokyo (JP)

( * ) Notice: Subject to any disclaimer, the term of this patent is extended or adjusted under 35 U.S.C. 154(b) by 14 days.

(21) Appl. No.: 15/672,202

(22) Filed: Aug. 8, 2017

(65) Prior Publication Data
US 2018/0045935 A1    Feb. 15, 2018

(30) Foreign Application Priority Data
Aug. 9, 2016    (JP) .................. 2016-156411

(51) Int. Cl.
*G02B 21/06*     (2006.01)
*G02B 21/00*     (2006.01)
(Continued)

(52) U.S. Cl.
CPC ........... *G02B 21/006* (2013.01); *C12M 41/36* (2013.01); *C12M 41/48* (2013.01); *G02B 21/008* (2013.01);
(Continued)

(58) Field of Classification Search
CPC ............. G02B 21/00; G02B 21/0004; G02B 21/0008; G02B 21/002; G02B 21/0024;
(Continued)

(56) References Cited

U.S. PATENT DOCUMENTS 5,595,708 A * 1/1997 Berndt ............. G01N 21/253
356/337
7,148,043 B2 * 12/2006 Kordunsky ............ B01L 7/52
435/91.2

(Continued)

FOREIGN PATENT DOCUMENTS

| JP | 2005-295818 | 10/2005 |
| WO | WO 2011/090792 | 7/2011 |
| WO | WO 2015/174356 | 11/2015 |

OTHER PUBLICATIONS

Extended European Search Report to corresponding European Patent Application No. 17185310.4, dated Jan. 22, 2018 (11 pgs.).

*Primary Examiner* — Arnel C Lavarias
(74) *Attorney, Agent, or Firm* — John C. Pokotylo; Pokotylo Patent Services

(57) ABSTRACT

An observation apparatus includes an imaging unit that includes an imaging section and an illumination section, a driving mechanism that moves the imaging unit, a position control section, a vessel position acquisition section, an illumination control section, an imaging control section that causes the imaging section to image a sample. The illumination section includes a plurality of emitting sections configured to emit illumination light and illuminates the sample. The position control section and the vessel position acquisition section acquire position information on the imaging unit and the sample, respectively. The illumination control section selects which of the emitting sections emits illumination light and causes the selected emitting section to emit main illumination light based on the position information on the sample and the imaging unit.

20 Claims, 18 Drawing Sheets

(51) Int. Cl.
*G02B 21/26* (2006.01)
*G02B 21/36* (2006.01)
*C12M 1/34* (2006.01)
*C12M 1/36* (2006.01)

(52) U.S. Cl.
CPC .......... *G02B 21/26* (2013.01); *G02B 21/365* (2013.01); *G02B 21/367* (2013.01)

(58) Field of Classification Search
CPC ............ G02B 21/0032; G02B 21/0052; G02B 21/006; G02B 21/008; G02B 21/06; G02B 21/08; G02B 21/084; G02B 21/086; G02B 21/088; G02B 21/12; G02B 21/24; G02B 21/26; G02B 21/36; G02B 21/361; G02B 21/362
USPC ....... 359/362, 363, 368, 369, 385, 387, 388, 359/390, 391, 392, 393
See application file for complete search history.

(56) References Cited

U.S. PATENT DOCUMENTS

| | | |
|---|---|---|
| 2009/0080611 A1 | 3/2009 | Ganz et al. |
| 2012/0195044 A1 | 8/2012 | Higuchi |
| 2013/0260445 A1 | 10/2013 | Oura et al. |
| 2017/0044481 A1 | 2/2017 | Kawano et al. |
| 2018/0025475 A1* | 1/2018 | Kato .................. G02B 21/06 348/241 |

* cited by examiner

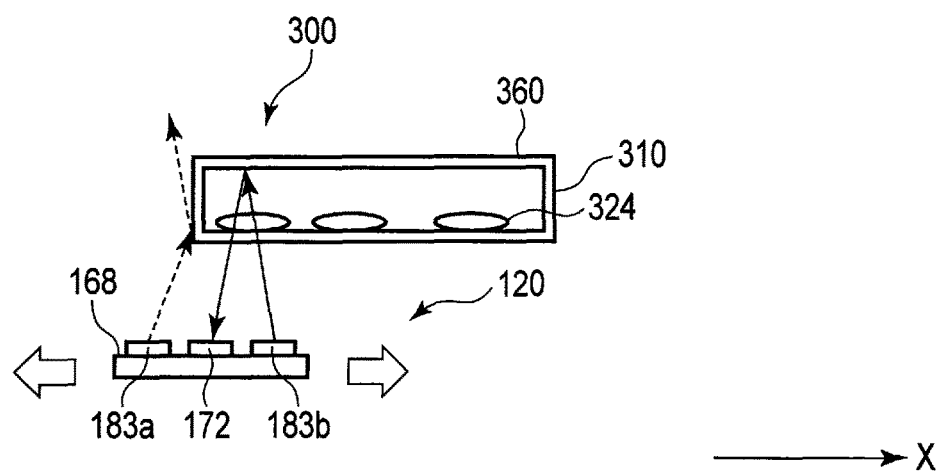
F I G. 5
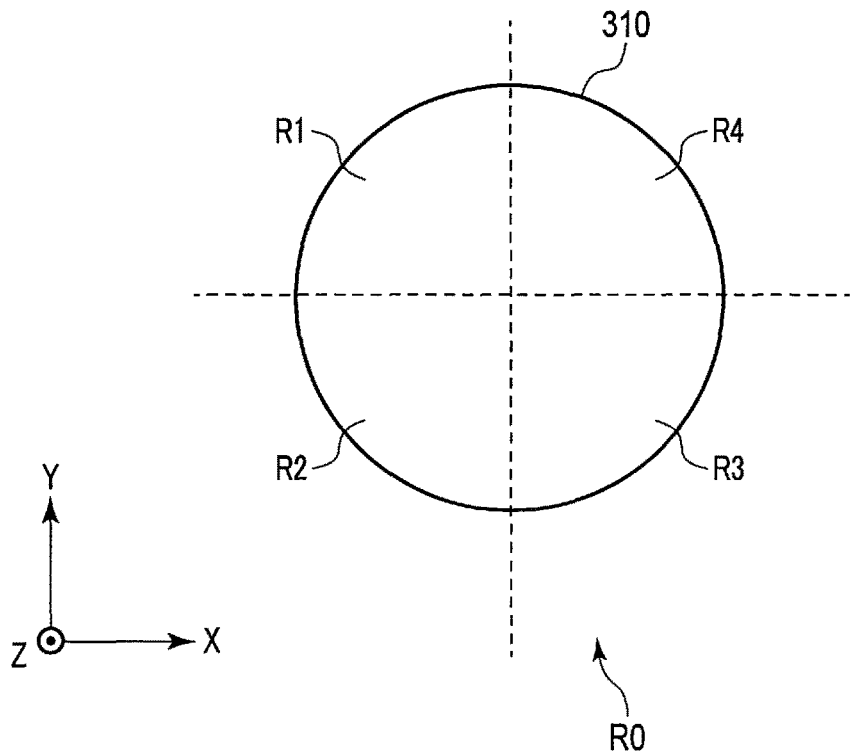
F I G. 6

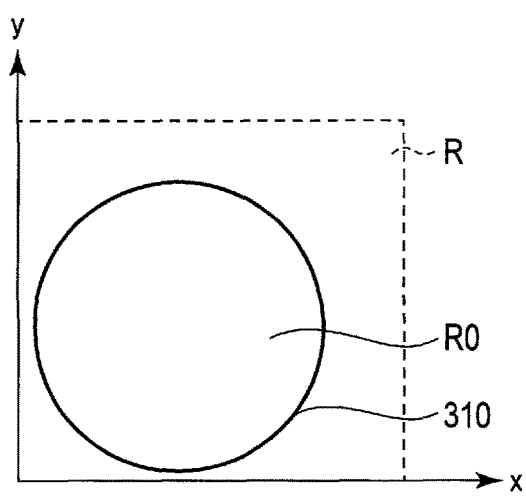
F I G. 8

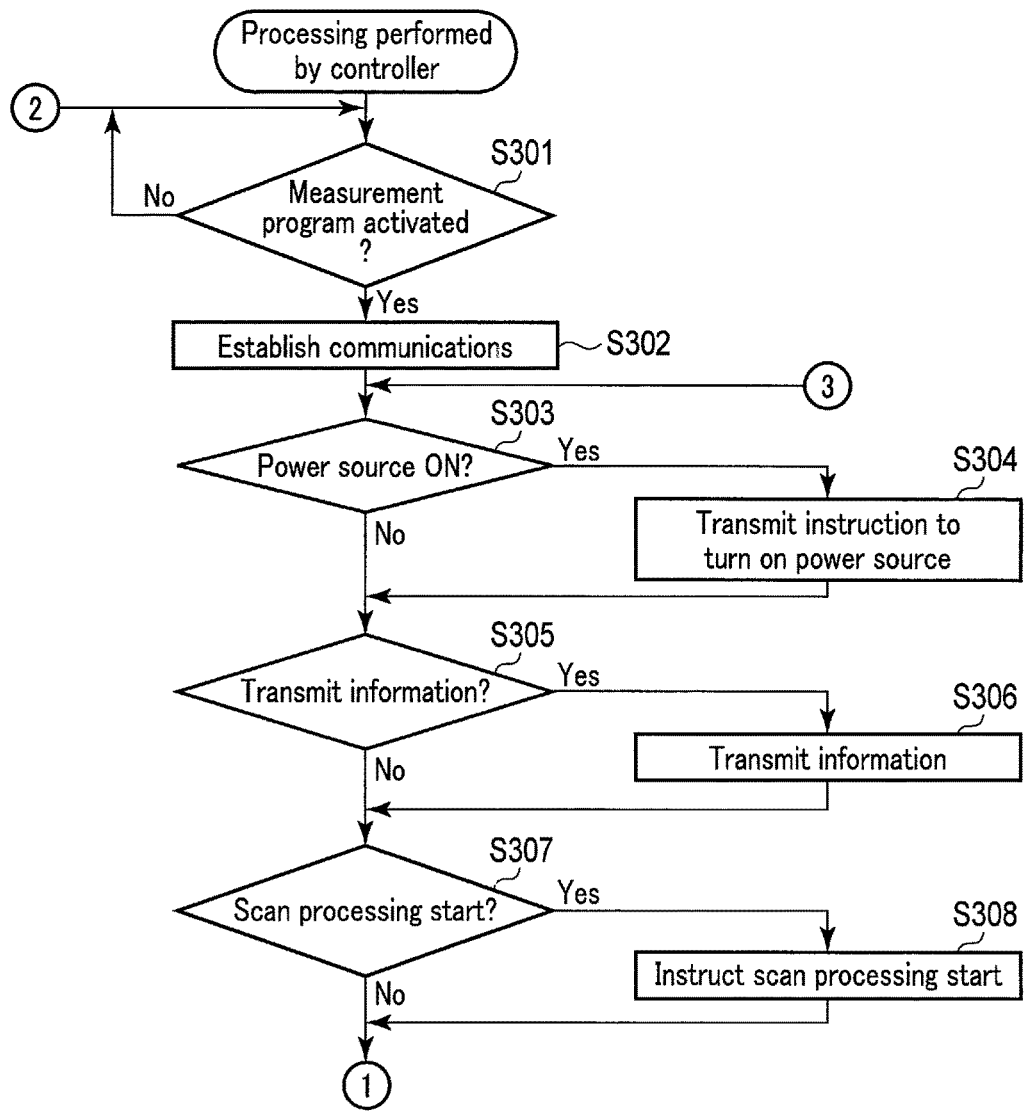
F I G. 11A

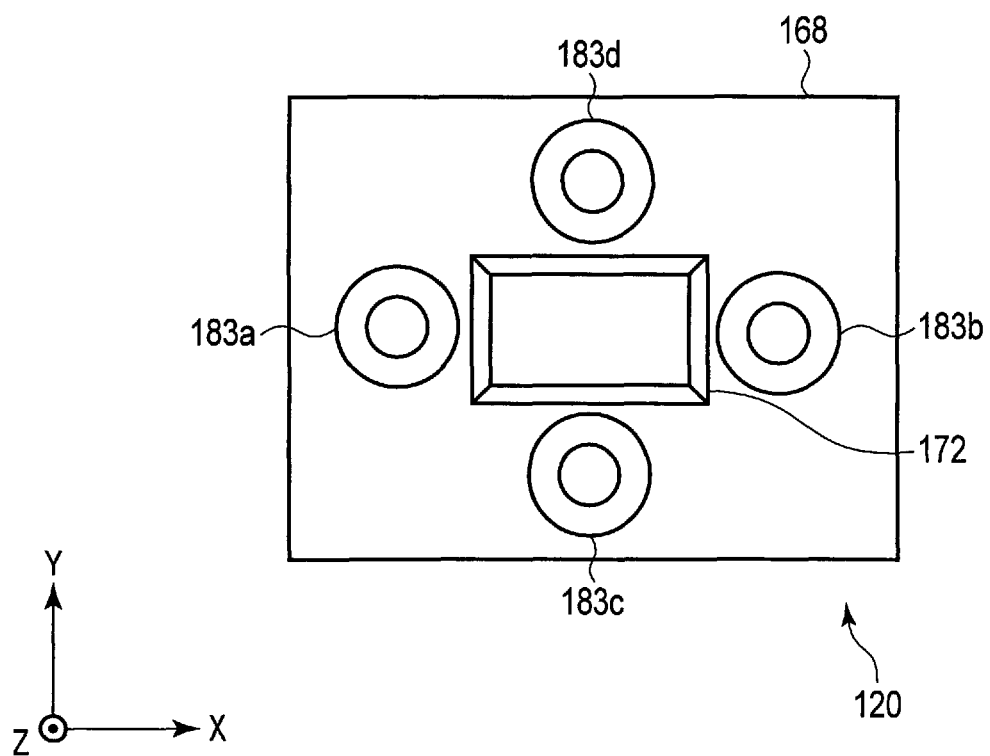
F I G. 12

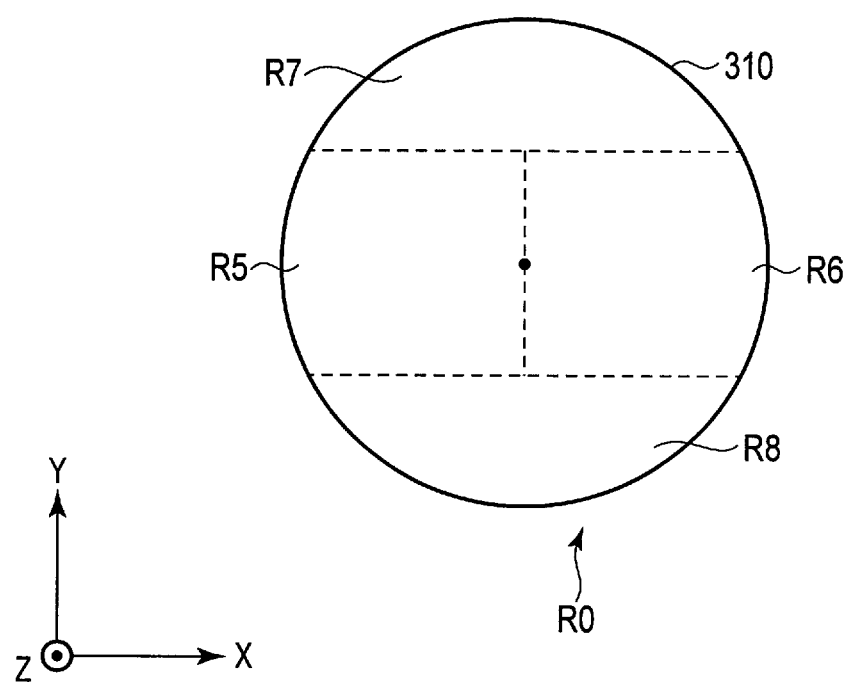
F I G. 13

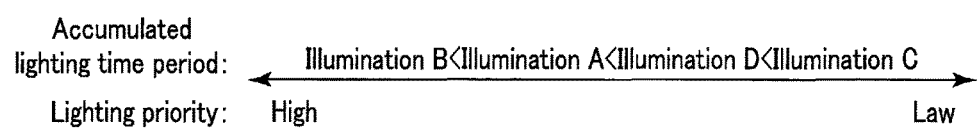
Accumulated lighting time period: Illumination B<Illumination A<Illumination D<Illumination C
Lighting priority: High                                                                                          Law
F I G. 16
|  | Illumination A | Illumination B | Illumination C | Illumination D |
|---|---|---|---|---|
| 1st area |  | ○ | ◎ |  |
| ⇩ |  |  |  |  |
| 4th area | ○ |  | ◎ |  |
| ⇩ |  |  |  |  |
| 3rd area | ○ |  |  | ◎ |
| ⇩ |  |  |  |  |
| 2nd area |  | ○ |  | ◎ |
F I G. 17

|  | Illumination A | Illumination B | Illumination C | Illumination D |
|---|---|---|---|---|
| 1st area |  | ◎ | ○ |  |
| ⇩ |  |  |  |  |
| 4th area | ◎ |  | ○ |  |
| ⇩ |  |  |  |  |
| 3rd area | ◎ |  |  | ○ |
| ⇩ |  |  |  |  |
| 2nd area |  | ◎ |  | ○ |
| ⇩ |  |  |  |  |
| 1st area |  | ◎ | ○ |  |
| ⇩ |  |  |  |  |
| 4th area | ◎ |  | ○ |  | ← T1
| ⇩ |  |  |  |  |
| 3rd area | ○ |  |  | ◎ | ← T2
| ⇩ |  |  |  |  |
| 2nd area |  | ○ |  | ◎ |

F I G. 18

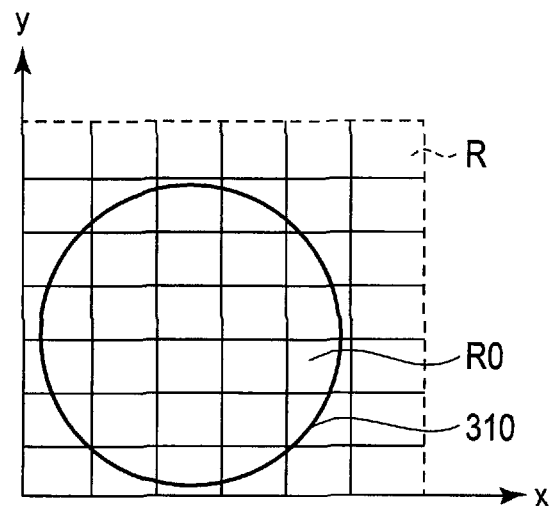
F I G. 19
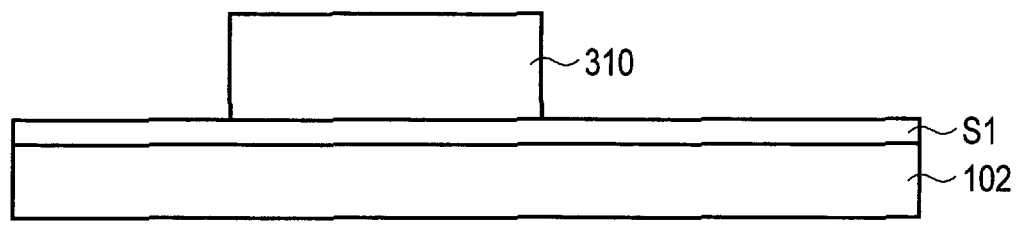
F I G. 20

OBSERVATION APPARATUS, METHOD FOR CONTROLLING OBSERVATION APPARATUS, AND NON-TRANSITORY COMPUTER READABLE STORAGE MEDIUM STORING CONTROL PROGRAM FOR OBSERVATION APPARATUS

CROSS-REFERENCE TO RELATED APPLICATIONS

This application is based upon and claiming the benefit of priority from prior Japanese Patent Application No. 2016-156411, filed Aug. 9, 2016, the entire contents of which are incorporated herein by reference.

BACKGROUND OF THE INVENTION

1. Field of the Invention

The present invention relates to an observation apparatus, a method for controlling an observation apparatus, and a non-transitory computer-readable storage medium storing a control program for an observation apparatus.

2. Description of the Related Art

In general, an apparatus wherein a culture vessel is statically placed in an incubator and images of cultured cells or the like in the culture vessel are taken, is known in the art. For example, Jpn. Pat. Appln. KOKAI Publication No. 2005-295818 discloses a technique related to an apparatus which takes a number of images while moving a camera (imaging section) inside an incubator so as to take images of cells existing in a wide range of a culture vessel.

BRIEF SUMMARY OF THE INVENTION

According to an aspect of the invention, an observation apparatus includes an imaging unit including an imaging section that includes an imaging optical system and an image sensor and that images a sample to output an image signal, and an illumination section that includes a plurality of emitting sections which are configured to emit illumination light and are located away from an optical axis of the imaging optical system and that illuminates the sample, a driving mechanism that moves the imaging unit, and at least one control circuit which acquires position information on the imaging unit, acquires position information on the sample, selects which of the emitting sections emits illumination light based on the position information on the sample and the position information on the imaging unit, causes the selected emitting section to emit main illumination light, and causes the imaging section to perform imaging.

According to an aspect of the invention, a method for controlling an observation apparatus is provided. The observation apparatus includes an imaging unit including an imaging section that includes an imaging optical system and an image sensor and that images a sample to output an image signal, and including an illumination section that includes a plurality of emitting sections which are configured to emit illumination light and are located away from an optical axis of the imaging optical system and that illuminates the sample, and a driving mechanism that moves the imaging unit. The method includes causing the driving mechanism to move the imaging unit, acquiring position information on the imaging unit, acquiring position information on the sample, selecting which of the emitting sections emits illumination light based on the position information on the sample and the position information on the imaging unit, causing the selected emitting section to emit main illumination light, and causing the imaging section to perform imaging.

According to an aspect of the invention, a non-transitory computer readable storage medium storing a control program for an observation apparatus is provided. The observation apparatus includes an imaging unit including an imaging section that includes an imaging optical system and an image sensor and that images a sample to output an image signal, and including an illumination section that includes a plurality of emitting sections which are configured to emit illumination light and are located away from an optical axis of the imaging optical system and that illuminates the sample, and a driving mechanism that moves the imaging unit. The control program causes a computer to execute causing the driving mechanism to move the imaging unit, acquiring position information on the imaging unit acquiring position information on the sample, selecting which of the emitting sections emits illumination light based on the position information on the sample and the position information on the imaging unit, causing the selected emitting section to emit main illumination light, and causing the imaging section to perform imaging.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5 is a view illustrating an example of a light path of illumination light and scattering in a vessel edge portion according to the first embodiment.

FIG. 6 is a diagram illustrating an example of an observation target range and a manner of division of the same in illumination control according to the first embodiment.

FIG. 8 is a diagram illustrating an example of an observable range, a vessel position, and an observation target range based on vessel type information according to the first embodiment.

FIG. 11A is a flowchart illustrating an example of processing performed by a controller according to the first embodiment.

FIG. 12 is a view illustrating an outline of a configuration example of an imaging unit according to a second embodiment.

FIG. 13 is a diagram illustrating an example of an observation target range and a manner of division of the same in illumination control according to a third embodiment.

FIG. 16 is a diagram illustrating an example of lighting priorities of illuminations under illumination control based on an accumulated lighting time period of each of the illuminations according to the fourth embodiment.

FIG. 17 is a diagram illustrating an example of illuminations selected under illumination control based on a movement locus of an imaging unit according to the fourth embodiment.

FIG. 18 is a diagram illustrating an example of illuminations selected in illumination control based on an accumulated lighting time period of each of the illuminations and a movement locus of the imaging unit according to the fourth embodiment.

FIG. 19 is a diagram illustrating an example of vessel position acquisition based on image information of a plurality of acquired images.

FIG. 20 is a diagram illustrating an example of vessel position acquisition based on sensor output information.

DETAILED DESCRIPTION OF THE INVENTION

First Embodiment

The first embodiment of the present invention will be explained with reference to the drawings. A measurement system of this embodiment is a system which takes images of a cell, a cell group, and a tissue which are being cultured, and which makes a record of the numbers of cells or cell groups and the form thereof. The technique of this embodiment realizes a measurement system configured to acquire position information on a vessel edge or the like to be observed and to perform imaging under appropriate illumination control based on the acquired information. The imaging may be a photography. The acquired image may be either a still image or a moving image.

<Configuration of Measurement System>

Figure 1:
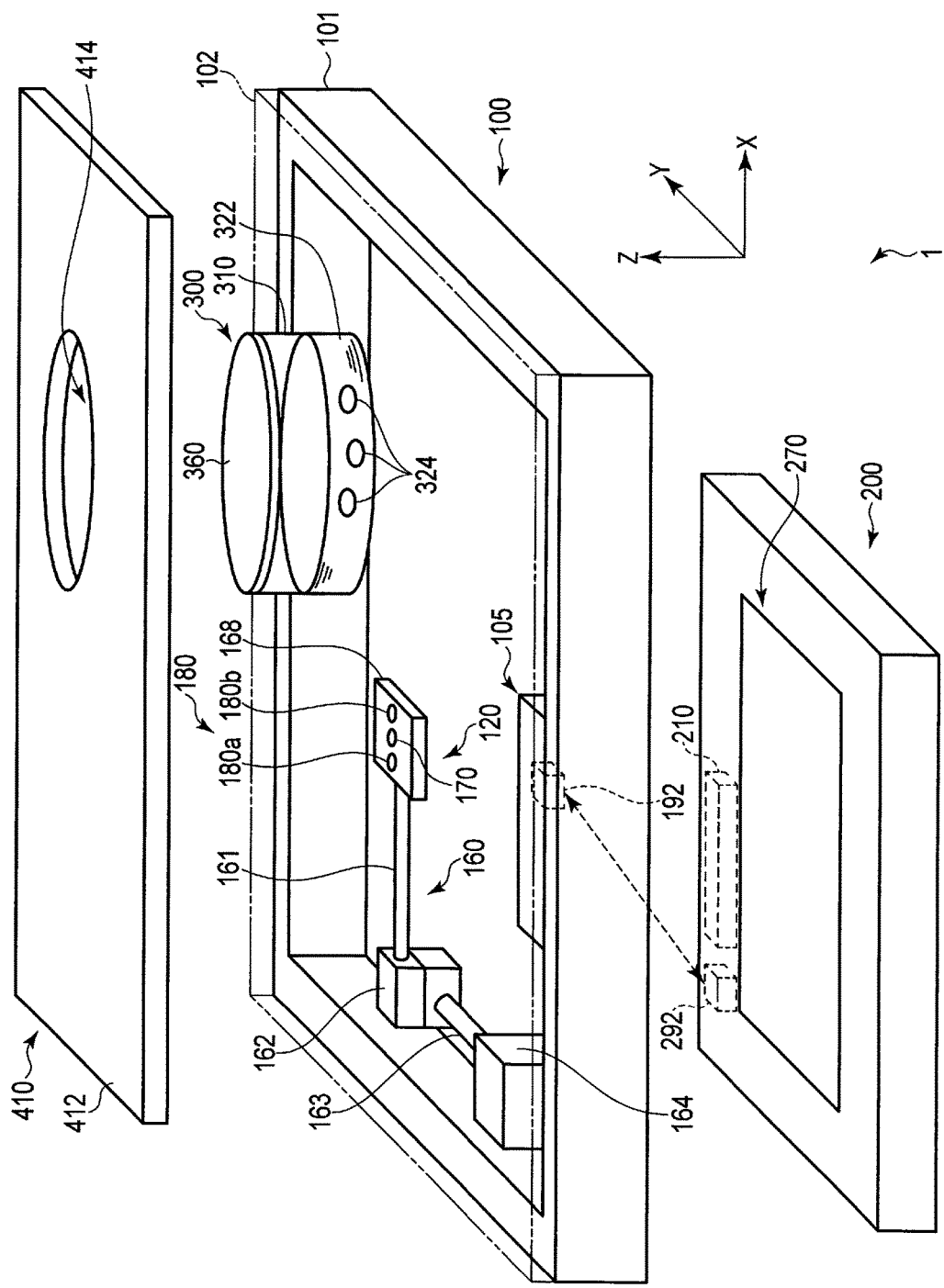
FIG. 1 is a schematic view illustrating an outline of the appearance of a measurement system according to a first embodiment.
Figure 2:
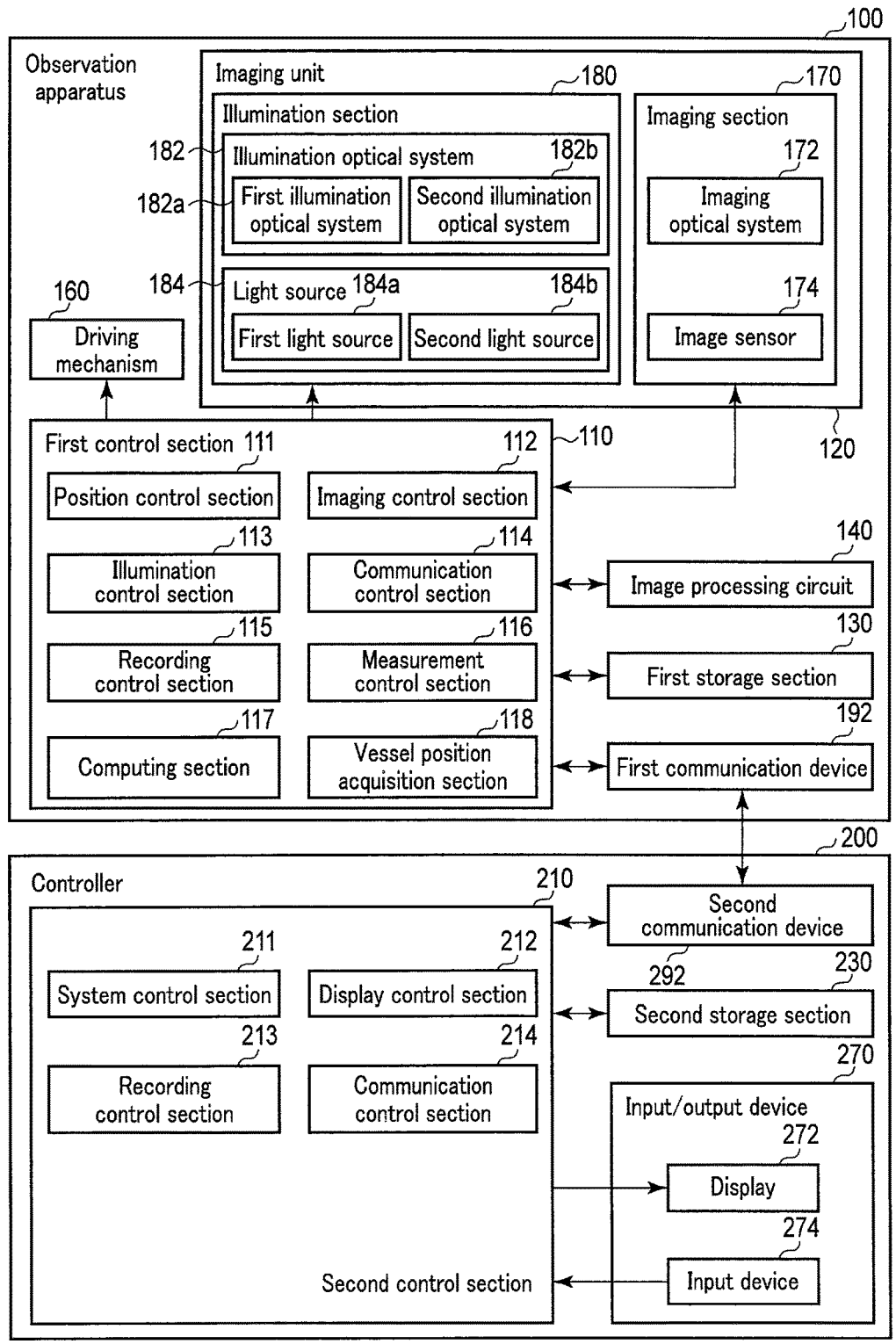
FIG. 2 is a block diagram illustrating an outline of a configuration example of the measurement system according to the first embodiment.

FIG. 1 is a schematic view illustrating an outline of the appearance of a measurement system 1. FIG. 2 is a block diagram illustrating a configuration example of the measurement system 1. The measurement system 1 includes an observation apparatus 100 and a controller 200. As shown in FIG. 1, the observation apparatus 100 is approximately plate-shaped. The observation apparatus 100 is provided, for example, inside an incubator, and a sample 300 to be observed is arranged on top of the observation apparatus 100. For the sake of explanation, an x-axis and a y-axis perpendicular to each other are defined in a plane parallel to the surface of the observation apparatus 100 on which the sample 300 is arranged, and a z-axis is defined as an axis perpendicular to both the x-axis and the y-axis. A transparent plate 102 is placed as a top plate of the observation apparatus 100, and an imaging section 170 is provided inside a casing 101 of the observation apparatus 100. The observation apparatus 100 takes an image of the sample 300, via the transparent plate 102 interposed, and the image of the sample 300 is acquired thereby. On the other hand, the controller 200 is provided, for example, on the outside of the incubator. The observation apparatus 100 and the controller 200 communicate with each other. The controller 200 controls operations of the observation apparatus 100.

(Sample)

An example of the sample 300 to be observed by the measurement system 1 will be described below. A culture medium 322 is in a vessel 310, and cells 324 are cultured in the culture medium 322. The vessel 310 may be, for example, a petri dish, a culture flask, a multiwell plate, or the like. The vessel 310 is a culture vessel for culturing a biological sample, for example. The vessel 310 is not limited to any specific shape or size. The vessel 310 is, for example, a transparent vessel having a surface or part that is transparent to illumination light. The culture medium 322 may be either a liquid medium or a solid medium. The cells 324 to be measured may be either adhesive cells or floating cells. Alternatively, the cells 324 may be spheroids or tissues. In addition, the cells 324 may be derived from any organism or may be bacteria or the like. As described above, the sample 300 includes a living sample which is either the living substance itself or is derived from the living substance.

(Observation Apparatus)

As shown in FIG. 1, the transparent plate 102 made of, for example, glass, is provided on top of the casing 101 of the observation apparatus 100. The sample 300 is statically placed on this transparent plate 102. Although FIG. 1 shows that the top plate of the casing 101 is entirely transparent, the observation apparatus 100 may be designed so that part of the top plate of the casing 101 is a transparent plate, and the remaining part of the top plate is opaque.

The transparent plate 102 may be overlaid with a fixing frame 410 to determine the position where the sample 300 is placed on the transparent plate 102 and to fix the sample 300. The fixing frame 410 may be designed so that it is arranged at a specific position with respect to the transparent plate 102. For example, the fixing frame 410 may have the same size as the transparent plate 102. The fixing frame 410 includes a fixing plate 412 and a hole 414 formed in the fixing plate 412. The hole 414 has a diameter slightly larger than the outer diameter of the vessel 310 of the sample 300. Therefore, in the state where the fixing frame 410 is placed on the transparent plate 102, the vessel 310 can be fixed in the hole 414. A plurality of fixing frames 410 of different types may be prepared in accordance with the types of vessels 310 of the sample 300. The fixing frame 410 may be employed; alternatively, it can be omitted. What is required in practice is merely that the fixing frame 410 has an element serving as a guide to locate the vessel 310 always at a specific position. The guide may be, for example, a projection, hole, groove, marker, or the like having a shape corresponding to the vessel 310. For example, the user may locate the vessel 310 to fit with a structure serving as the guide.

Various structural elements of the observation apparatus 100 are provided inside the casing 101. The interior of the incubator has a temperature of 37° C. and a humidity of 95%. Since the observation apparatus 100 is used in an environment of high ambient temperature and humidity, the casing 101 and the transparent plate 102 are designed to maintain airtightness. To protect the interior of the observation apparatus 100 from high-humidity environment, the inside enclosed by the casing 101 and the transparent plate 102 may have a higher pressure in comparison with the outside thereof.

An imaging unit 120 is provided inside the casing 101. As shown in FIG. 1 and FIG. 2, the imaging unit 120 includes a support section 168, the imaging section 170, and an illumination section 180. The imaging section 170 includes an imaging optical system 172 and an image sensor 174. The imaging section 170 takes an image of the region where the sample 300 is present, and thus acquires an image of the sample 300. The imaging section 170 generates an image signal or image data based on an image which is formed on an imaging plane of the image sensor 174 through the imaging optical system 172. The imaging optical system 172 is preferably a zoom optical system capable of changing its focal distance.

The illumination section 180 includes a first illumination section 180a and a second illumination section 180b. As shown in FIG. 1, the first illumination section 180a and the second illumination section 180b are provided near or around the imaging section 170 on both sides of the imaging section 170 in the support section 168. The illumination section 180 emits illumination light in the direction toward the transparent plate 102, namely, in the direction toward the sample 300. A part of the illumination section 180 that emits illumination light in the direction toward the sample 300 is hereinafter referred to as an emitting section.

As shown in FIG. 2, the illumination section 180 further includes an illumination optical system 182 and a light source 184. The illumination optical system 182 includes a first illumination optical system 182a and a second illumination optical system 182b. The light source 184 includes a first light source 184a and a second light source 184b. For example, the illumination light emitted from the first light source 184a illuminates the sample 300 through the first illumination optical system 182a. Similarly, the illumination light emitted from the second light source 184b illuminates the sample 300 through the second illumination optical system 182b. The emitting section, which emits the illumination light, may be, for example, a light source or a part of an illumination optical system.

Figure 3:
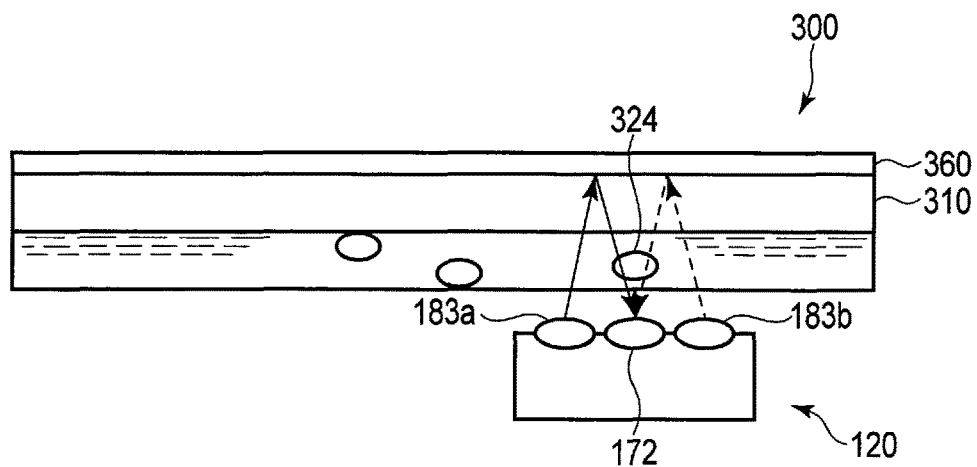
FIG. 3 is a side view illustrating an outline of a configuration example of a periphery of a sample according to the first embodiment.

FIG. 3 is a side view illustrating an outline of a configuration example of a periphery of the sample 300 according to the first embodiment. A configuration of the imaging unit 120 will be explained with reference to FIG. 3. As shown in FIG. 3, for example, when taking an image, the imaging unit 120 emits illumination light from at least one of a first emitting section 183a of the first illumination section 180a and a second emitting section 183b of the second illumination section 180b. The first emitting section 183a and the second emitting section 183b are located away from the optical axis of the imaging optical system 172, and on both sides of the imaging optical system 172. The emitting sections are preferably arranged, but are not limited to be symmetrical with respect to the imaging optical system 172. In the following, the description with only the term "emitting section" represents a case in which the emitting section may be any of the plurality of emitting sections. The description with only the term "illumination light" represents a case in which the illumination light may be emitted from any of the plurality of emitting sections. Furthermore, the illumination light may be emitted from either one emitting section or a plurality of emitting sections.

As shown in FIG. 3, a vessel top plate 360 is on top of the sample 300. The vessel top plate 360 reflects part of illumination light. As indicated by solid arrows in FIG. 3, for example, the illumination light emitted from the first emitting section 183a irradiates the vessel top plate 360. At this time, part of the illumination light is reflected by the vessel top plate 360 and part of the illumination light is transmitted through the vessel top plate 360. Part of reflected light illuminates the cell 324 and enters the imaging optical system 172 of the imaging section 170. Thus, the reflected light entering the imaging optical system 172 includes transmitted light transmitted through the cell 324. Illumination light emitted from the second emitting section 183b indicated by dashed arrows in FIG. 3 also illuminates the cell 324 and enters the imaging optical system 172, in the same manner as described above.

The illumination section 180 of the embodiment includes two illumination optical systems and two light sources; however, the number of illumination optical systems and light sources is not limited to two. For example, the number of illumination optical systems and light sources of the illumination section 180 may be more than two, and the numbers of illumination optical systems and the number of light sources may be different. Although the illumination section 180 is described as being arranged in the support section 168, what is required in practice is merely that the emitting sections of the respective illumination optical systems that emit illumination light are arranged in the support section 168. For example, the light sources may be arranged at any positions in the observation apparatus 100. A plurality of illumination optical systems having a common light source may be arranged in the support section 168. In this case, an optical system to switch the illumination optical systems that emit illumination light is provided. Thus, the imaging unit 120 includes at least the imaging optical system 172 and a plurality of emitting sections.

In this embodiment, the light source 184 is described as, but is not limited to, a light-emitting diode (LED). For example, the light source 184 may be a red light-emitting diode which affects cells less. More specifically, the light source 184 may be a red LED having an emission wavelength of 630 nm. The light source 184 may be a red light source configured to emit red light by using a fluorescent lamp or a mercury lamp. Thus, the illumination light emitted from the light source 184 may have any wavelength. For example, the wavelength of illumination light may fall within any of ultraviolet, visible, and infrared wavelength regions, depending on an object to be observed and an environment inside the incubator. Furthermore, each of the light sources may comprise a cooling mechanism.

Referring back to FIG. 1, the description will be continued. The imaging unit 120 is moved by a driving mechanism 160. The driving mechanism 160 is provided with an X feed screw 161 and an X actuator 162 for moving the imaging unit 120 in the X-axis direction. The driving mechanism 160 is also provided with a Y feed screw 163 and a Y actuator 164 for moving the imaging unit 120 in the Y-axis direction. The imaging section 170 can partly acquire an image of the sample 300 on the transparent plate 102 only on a one-by-one basis. However, by moving the imaging unit 120 with the driving mechanism 160, the imaging section 170 can acquire an image of a wide range.

The imaging position in the Z-axis direction is changed by changing the focus position of the imaging optical system 172 in an optical axis direction. In other words, the imaging optical system 172 is provided with a focus adjustment mechanism for moving a focusing lens in the optical axis direction. In place of the focus adjustment mechanism or in combination therewith, the driving mechanism 160 may be provided with a Z feed screw and a Z actuator for moving the imaging unit 120 in the Z-axis direction.

In this embodiment, an X-Y plane is defined in a plane parallel to the surface of the observation apparatus 100 on which the sample 300 is arranged, as described above. For the purpose of explanation in the following, the positive direction of the X-axis direction is referred to as an X+ direction, and defined as a direction away from the X actuator 162 along the longitudinal direction of the X feed screw 161. Similarly, the positive direction of the Y-axis direction is referred to as a Y+ direction, and defined as a direction away from the Y actuator 164 along the longitudinal direction of the Y feed screw 163. The positive direction of the Z-axis direction is referred to as a Z+ direction, and defined as a direction from the imaging unit 120 toward the sample 300. Furthermore, the negative direction of the X-axis direction, the negative direction of the Y-axis direction, and the negative direction of the Z-axis direction are respectively referred to as an X− direction, a Y− direction, and a Z− direction. In this embodiment, the imaging optical system 172 and the emitting sections are described as being arranged on a side of the imaging unit 120 facing the sample 300, that is, a surface on the side of the Z+ direction. However, the imaging optical system 172 and the emitting sections are not limited to this arrangement. The imaging optical system 172 and the emitting sections may be arranged to sandwich the sample 300 in the Z direction; for example, the imaging optical system 172 may be arranged on the side of the Z− direction of the sample 300 and a plurality of emitting sections may be arranged on the side of the Z+ direction of the sample 300. Advantages of the embodiment described below will be obtained even if such an arrangement is employed. In this embodiment, the first emitting section 183a is provided on a side of the X− direction of the imaging unit 120 and the second emitting section 183b is provided on a side of the X+ direction thereof.

A circuit group 105 for controlling the respective operations of the driving mechanism 160, the imaging section 170 and the illumination section 180 is provided inside the casing 101. A first communication device 192 is provided for the circuit group 105. The first communication device 192 is, for example, a device which communicates wirelessly with the controller 200. For example, wireless communications, such as Wi-Fi or Bluetooth are utilized for the communications. The observation apparatus 100 and the controller 200 may be connected by a wire, and wired communications may be carried out. As described above, the imaging section 170 that generates image data by imaging via the transparent plate 102 and the driving mechanism 160 that moves the imaging section 170 are provided inside the casing 101. Accordingly, the structure of the apparatus can be reliable, easy to handle and clean, and can prevent contamination or the like.

As shown in FIG. 2, the observation apparatus 100 includes a first control section 110, a first storage section 130, and an image processing circuit 140, in addition to the driving mechanism 160, the imaging unit 120, and the first communication device 192 described above. The first control section 110, the first storage section 130, the image processing circuit 140, and the first communication device 192 are arranged, for example, in the circuit group 105 described above.

The first control section 110 controls operations of each of the elements of the observation apparatus 100. The first control section 110 functions as a position control section 111, an imaging control section 112, an illumination control section 113, a communication control section 114, a recording control section 115, a measurement control section 116, a computing section 117, and a vessel position acquisition section 118. The position control section 111 controls the driving mechanism 160 to control the position of the imaging unit 120. The position control section 111 acquires a position of the imaging unit 120 that is moved by the driving mechanism 160. The imaging control section 112 controls operations of the imaging section 170 to cause the imaging section 170 to acquire an image of the sample 300. The illumination control section 113 controls operations of the illumination section 180. The communication control section 114 controls the communications with the controller 200 that are performed by using the first communication device 192. The recording control section 115 controls the recording of data obtained by the observation apparatus 100. The measurement control section 116 controls the overall measurement, including measurement timing and the number of times the measurement is performed. The computing section 117 performs various analyses based on the image acquired by the imaging section 170, a brightness value, etc. The vessel position acquisition section 118 acquires position information on the sample 300. The position information is acquired based on, for example, vessel type information input by the user, image data, a sensor output value, etc.

The first storage section 130 stores, for example, programs and various parameters for use in the first control section 110. The first storage section 130 also stores data obtained by the observation apparatus 100.

The image processing circuit 140 performs various kinds of image processing for the image data generated by the imaging section 170. After the image processing by the image processing circuit 140, data is, for example, stored in the first storage section 130 or transmitted to the controller 200 by way of the first communication device 192. The first control section 110 or the image processing circuit 140 may perform various kinds of analysis, based on the obtained image. For example, the first control section 110 or the image processing circuit 140 extracts an image of a cell or cell group included in the sample 300, counts the number of cells or cell groups, or calculates a shape or size thereof, based on the obtained image. The results of the analysis thus obtained are, for example, stored in the first storage section 130 or transmitted to the controller 200 by way of the first communication device 192. The processing performed by the image processing circuit 140 may be performed by the computing section 117.

Figure 4:
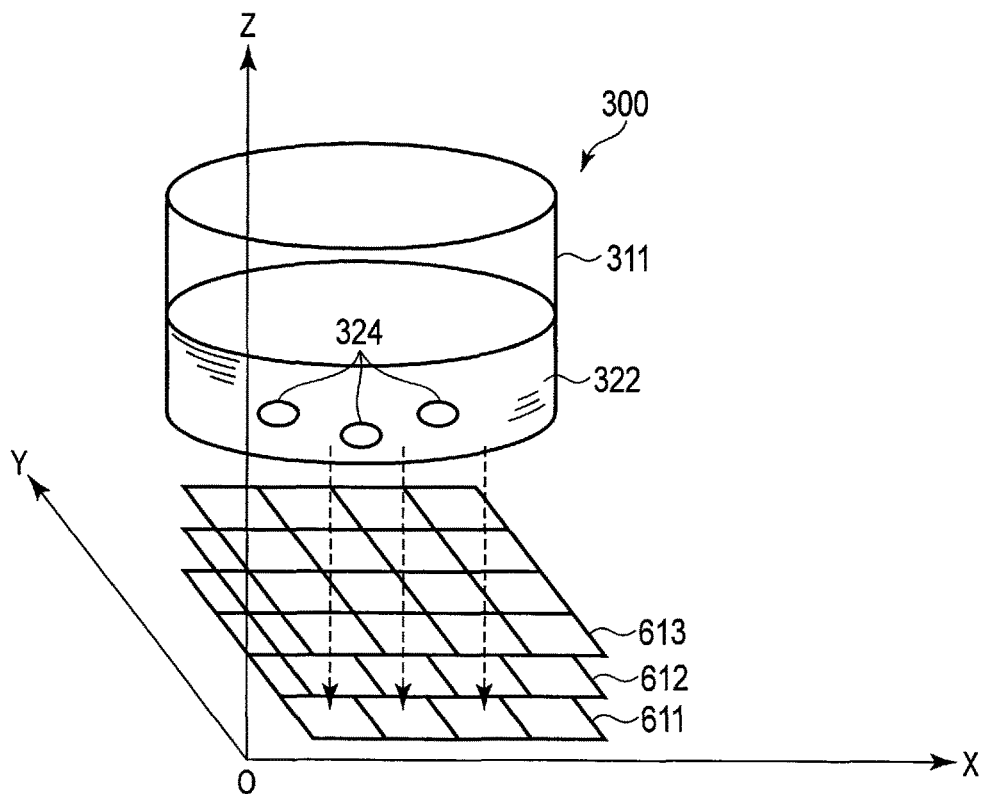
FIG. 4 is a view illustrating an example of image acquisition by an observation apparatus according to the first embodiment.

The imaging section 170 performs an imaging operation for light entering the imaging optical system 172, as described above with reference to FIG. 3. FIG. 4 is a view illustrating an example of image acquisition by the observation apparatus 100 according to the first embodiment. Image acquisition by the imaging section 170 will be explained with reference to FIG. 4. The observation apparatus 100 repeatedly takes an image, while changing its position in the X direction and the Y direction, for example, in a first plane, and a plurality of images are acquired thereby. The image processing circuit 140 synthesizes these images, thereby preparing one first image 611 of the first plane. The first plane is, for example, a plane perpendicular to the optical axis of the imaging section 170, that is, a plane parallel to the transparent plate 102. Also, the observation apparatus 100 changes the imaging position in the thickness direction to a second plane and to a third plane, and repeatedly takes an image, while changing its position in the X direction and Y direction in each of the planes. The images are synthesized, so that a second image 612 and a third image 613 are acquired. The thickness direction is the Z-axis direction, namely, the optical axis direction of the imaging section 170, and is perpendicular to the transparent plate 102. In this manner, an image at each three-dimensional position is acquired.

In the above, a description was given of an example in which an image is repeatedly taken, with the imaging plane being changed in the Z direction. Instead, an image may be repeatedly taken, with the imaging plane being changed only in the X direction and the Y direction without obtaining a plurality of images in the Z direction. In this case, a synthesis image of one plane is obtained. In the method for acquiring the first image 611, the second image 612 and the third image 613, a scan may be performed in the X direction and Y direction, with the position in the Z-axis direction being kept fixed, and after changing the position in the Z-axis direction, a scan may be performed in the X direction and Y direction. Alternatively, an image of a given position in the X direction and Y direction may be taken a number of times, with the position being changed in the Z-axis direction, and this operation may be performed, with the scan position being changed in the X direction and Y direction.

In imaging for measurement, the sample 300 need not be continuously irradiated with illumination light. The sample 300 may be irradiated with illumination light only at the instant of imaging. Due to the shortened irradiation time, the damage to the cell 324 can be reduced. Thus, the sample 300 can be irradiated with illumination light of sufficient intensity at the timing of imaging. This matter contributes to obtaining a quality image.

As described above, the imaging section 170 repeatedly takes an image, while changing its position in the X direction and the Y direction, thereby acquiring a plurality of images. However, during this image acquisition time, if the illumination light scatters, for example, at a vessel edge portion, the imaging section 170 cannot acquire appropriate images. FIG. 5 is a view illustrating an example of a light path of illumination light and scattering at a vessel edge portion according to the first embodiment. Scattering of illumination light at the vessel edge portion will be explained with reference to FIG. 5. The relative position of the imaging unit 120 with respect to the sample 300 may be changed by movement of the imaging unit 120 by the driving mechanism 160. Therefore, the relative position between the sample 300 and the imaging unit 120 shown in FIG. 3 may be changed to the relative position shown in FIG. 5.

When the sample 300 and the imaging unit 120 have the relative position shown in FIG. 5, the illumination light emitted from the first emitting section 183a travels through the light path indicated by the dashed arrows in FIG. 5. The illumination light mostly scatters, for example, at an edge portion of the vessel 310 that falls within the optical path, without being incident on the vessel top plate 360. Therefore, the imaging section 170 cannot sufficiently receive the illumination light and cannot acquire a satisfactory image. At this time, the illumination light emitted from the second emitting section 183b travels through the light path indicated by the solid arrows in FIG. 5. The illumination light can enter the imaging optical system 172 as described above with reference to FIG. 3, and the imaging section 170 can acquire an appropriate image.

The first control section 110 of this embodiment performs illumination control of appropriately selecting an emitting section that emits illumination light so that the illumination light does not scatter at the edge portion of the vessel 310, based on position information on the vessel 310 of the sample 300 and position information on the imaging unit 120. In the illumination control, the first control section 110 causes, for example, an emitting section within an area corresponding to the vessel 310 to emit the illumination light. The measurement system 1 of this embodiment can perform imaging, while maintaining an appropriate illumination environment by the illumination control. Furthermore, switching between the emitting sections to select an appropriate emitting section that emits illumination light can, at the same time, reduce wasteful emission of illumination light. The technique of this embodiment contributes to not only saving of energy necessary for using the observation apparatus 100, but also to reducing the amount of heat generation.

An example of illumination control based on position information on the sample 300 and the imaging unit 120 will be described. In this embodiment, the user selects a vessel 310 to be used in accordance with the vessel type information recorded in advance, and locates the vessel 310 to a designated position of the observation apparatus 100. The vessel type information includes, for example, types of vessels 310, a shape and size of each vessel 310, and position information on arrangement of each vessel 310 in the observation apparatus 100. The vessel type information is stored in the first storage section 130 or the second storage section 230.

FIG. 6 is a diagram illustrating an example of an observation target range and a manner of division of the same in the illumination control according to the first embodiment. A range to be observed by the observation apparatus 100, that is, an observation target range and a manner of division of the same, will be explained with reference to FIG. 6. In the explanation, a case in which the entire vessel 310 is observed will be explained. The first control section 110 determines an observation target range R0 based on the vessel type information relating to the vessel 310 determined by the user. The observation target range R0 may be referred to as a scan range. For example, when the user selects a circular dish, the circular observation target range R0 shown in FIG. 6 is determined. Then, the first control section 110 divides the observation target range R0 into a plurality of areas. For example, as shown in FIG. 6, in an area in an X– direction relative to the center of the vessel, an area in a Y+ direction relative to the center of the vessel is referred to as a first area R1 and an area in a Y– direction relative to the center of the vessel as a second area R2. For example, in an area in an x+ direction relative to the center of the vessel, an area in the Y– direction relative to the center of the vessel is referred to as a third area R3, and an area in the Y+ direction relative to the center of the vessel as a fourth area R4.

The first control section 110 acquires a current position of the imaging unit 120, and determines to which of the first area R1 to the fourth area R4 the current imaging range belongs, based on position information on the acquired current position and the position information on the vessel 310. The first control section 110 selects an emitting section that emits the illumination light based on the region where the imaging unit 120 is located.

For example, when the imaging unit 120 images a position included in the first area R1 or the second area R2, the first control section 110 causes the second emitting section 183b to emit the illumination light. The selection of the emitting section is based on the fact that, for example, when the imaging unit 120 scans the first area R1 and the second area R2, the second emitting section 183b is nearer to the center of the vessel 310 than the first emitting section 183a. The emitting section nearer to the center of the vessel 310 is selected to prevent the illumination light emitted from the emitting section from scattering at the vessel edge portion when imaging the vessel edge portion or a neighborhood thereof as described above with reference to FIG. 5. Similarly, when imaging a position in the third area R3 or the fourth area R4, the first control section 110 causes the first emitting section 183a to emit the illumination light. At this time, for example, the illumination light emitted from the first emitting section 183a may be used as supplementary illumination in the first area R1 and the second area R2, and the illumination light emitted from the second emitting section 183b may be used as supplementary illumination in the third area R3 and the fourth area R4. The illumination light as the supplementary illumination has a lesser amount of light as compared to the illumination light as the main illumination.

Rules of the illumination control are stored in, for example, the first storage section 130 or the second storage section 230. The observation target range R0 is described as being divided into the four areas to perform illumination control. However, the number of the divided areas is not limited to four. The number of divided areas may be more than one, for example, two or eight. Furthermore, the number of divided areas may be different from the number of emitting sections. The number of divided areas may be changed as needed in accordance with the type of a vessel or an observation target.

(Controller)

The controller 200 is, for example, a personal computer (PC) or a tablet type information terminal. In FIG. 1, a tablet type information terminal is depicted.

The controller 200 is provided with an input/output device 270 including a display 272 such as a liquid crystal display, and an input device 274 such as a touch panel. The input device 274 is not limited to the touch panel but may include a switch, a dial, a keyboard, a mouse, etc.

The controller 200 is also provided with a second communication device 292. The second communication device 292 is a device which communicates with the first communication device 192. The observation apparatus 100 and the controller 200 communicate with each other through the first communication device 192 and the second communication device 292.

The controller 200 is further provided with a second control section 210 and a second storage section 230. The second control section 210 controls operations of each of the elements of the controller 200. The second storage section 230 stores, for example, programs and various parameters for use in the second control section 210. The second storage section 230 also stores data obtained by and received from the observation apparatus 100.

The second control section 210 functions as a system control section 211, a display control section 212, a recording control section 213 and a communication control section 214. The system control section 211 performs various operations for controlling the measurement of the sample 300. The display control section 212 controls operations of the display 272. The display control section 212 causes the display 272 to display the necessary information. The recording control section 213 controls the recording of information in the second storage section 230. The communication control section 214 controls the communications with the observation apparatus 100 that are performed using the second communication device 292.

Each of the first control section 110, the image processing circuit 140, and the second control section 210 incorporates an integrated circuit such as a central processing unit (CPU), an application specific integrated circuit (ASIC), a field programmable gate array (FPGA), or a graphic processing unit (GPU). Each of the first control section 110, the image processing circuit 140, and the second control section 210 may be constituted by a single integrated circuit or by a combination of a number of integrated circuits. The first control section 110 and the image processing circuit 140 may be made by a single integrated circuit. Each of the position control section 111, the imaging control section 112, the illumination control section 113, the communication control section 114, the recording control section 115, the measurement control section 116, the computing section 117, and the vessel position acquisition section 118 of the first control section 110 may be constituted by a single integrated circuit or by a combination of a number of integrated circuits. Two or more of the position control section 111, the imaging control section 112, the illumination control section 113, the communication control section 114, the recording control section 115, the measurement control section 116, the computing section 117, and the vessel position acquisition section 118 may be constituted by a single integrated circuit or the like. Likewise, each of the system control section 211, the display control section 212, the recording control section 213, and the communication control section 214 of the second control section 210 may be constituted by a single integrated circuit or by a combination of a number of integrated circuits. Two or more of the system control section 211, the display control section 212, the recording control section 213, and the communication control section 214 may be constituted by a single integrated circuit or the like. The operations of these integrated circuits are executed, for example, in accordance with programs stored in the first storage section 130 or the second storage section 230, or in accordance with the programs stored in the storage regions of the integrated circuits.

<Operations of Measurement System>

Figure 7:
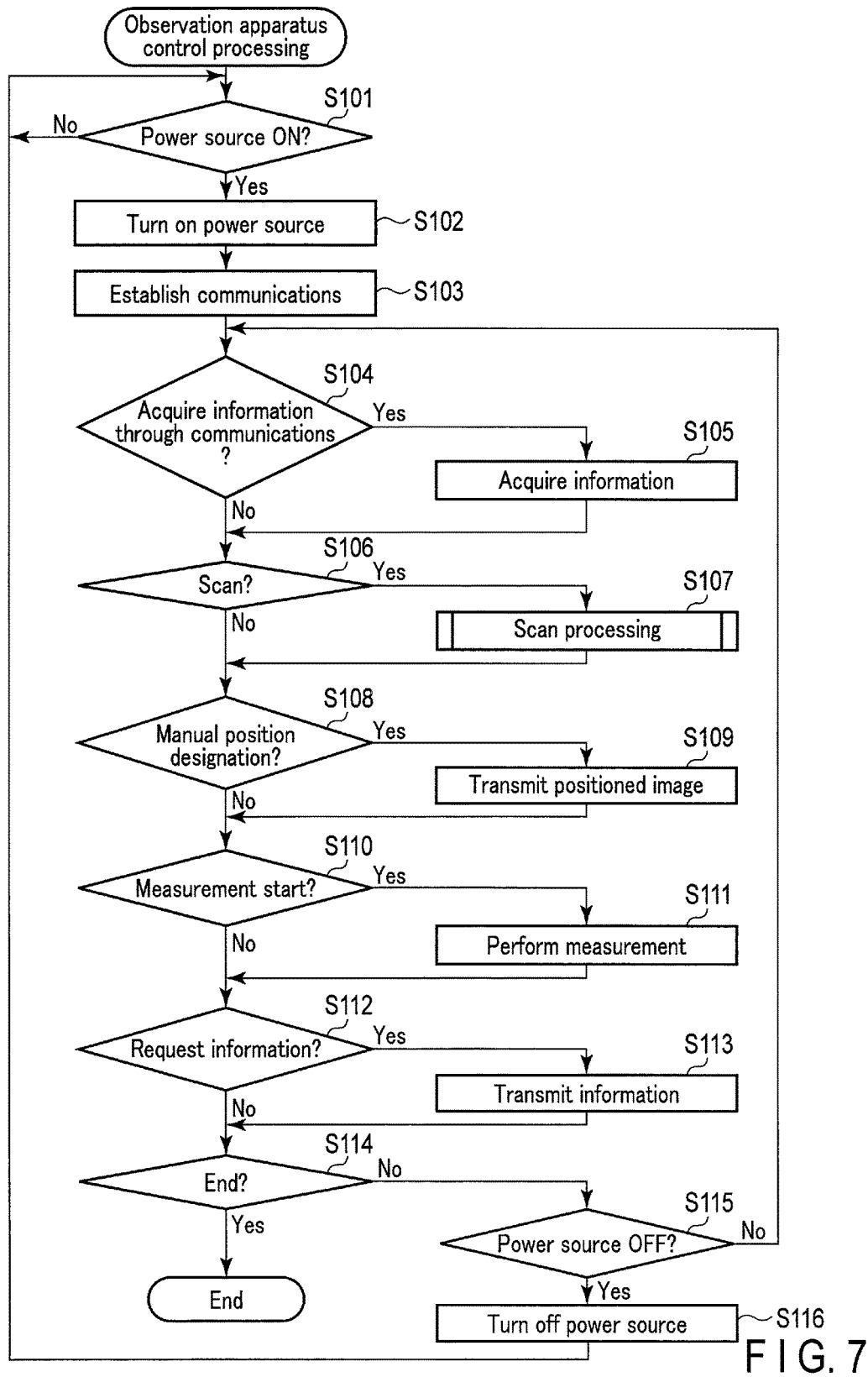
FIG. 7 is a flowchart illustrating an example of observation apparatus control processing according to the first embodiment.

Operations of the measurement system 1 will be described. FIG. 7 illustrates an example of observation apparatus control processing according to the first embodiment. Operations of the observation apparatus 100 will be described with reference to the flowchart shown in FIG. 7. The observation apparatus control processing starts when the observation apparatus 100, the controller 200, and the sample 300 are in place and preparations for measurement have been made.

In step S101, the first control section 110 determines whether or not the power source should be turned on. Where the power source is configured to be switched on at predetermined times, and when the predetermined times come, the first control section 110 determines that the power source should be turned on. Where the observation apparatus 100 constantly communicates with the controller 200 through low-power-consumption communication means such as Bluetooth Low Energy, and when the observation apparatus 100 receives instructions to turn on the power source from the controller 200 through the communication means, it is determined that the power source should be turned on. Unless the power source is turned on, the observation apparatus control processing stands by, repeating step S101. If it is determined that the power source should be turned on, the observation apparatus control processing advances to step S102.

In step S102, the first control section 110 turns on the power source to supply power to the respective portions of the observation apparatus 100. If the power source is turned on only when needed, for example, only when the sample 300 is actually measured, power saving can be attained. In particular, if the power source of the observation apparatus 100 is a battery, advantages can be obtained, for example, the driving time of the observation apparatus 100 can be lengthened. On the other hand, the first control section 110 may determine if power consumed by operations of turning on and off the power source is greater than standby energy, for example, if imaging intervals set in the apparatus are short, to suppress power consumption as a whole.

In step S103, the first control section 110 establishes communications with the controller 200. The communication means used in the embodiment is high-speed communication means, such as Wi-Fi.

In step S104, the first control section 110 determines whether or not information should be acquired from the controller 200 through the established communications. For example, when information is transmitted from the controller 200, it is determined that the information should be acquired. Unless the information is acquired, the observation apparatus control processing advances to step S106. If the information is acquired, the observation apparatus control processing advances to step S105.

In step S105, the first control section 110 acquires the information transmitted from the controller 200. The acquired information includes the above-mentioned vessel type information, condition information, such as measurement conditions (including imaging conditions, imaging intervals, and other parameters), a method for recording measurement results, a transmission condition for the measurement results, etc. After the first control section 110 acquires the information including the vessel type information transmitted from the controller 200, the observation apparatus control processing advances to step S106. FIG. 8 illustrates an example of an observable range R, a vessel position, and an observation target range R0 based on the vessel type information according to the first embodiment. The observable range R is an area in which observation, imaging, and measurement can be performed by the measurement system 1. The observable range R may vary depending on a size of the casing 101 of the observation apparatus 100 and a movable range of the imaging unit 120. As shown in FIG. 8, the vessel 310 is arranged within the observable range R in the observation apparatus 100 by means of, for example, the fixing frame 410. The first control section 110 determines the observation target range R0 based on the vessel type information, as described above with reference to FIG. 6. Thus, if the vessel 310 is appropriately arranged, the actual position of the vessel 310 coincides with the observation target range R0.

In step S106, the first control section 110 determines whether or not a scan should be performed. If it is determined in step S106 that the scan should not be performed, the observation apparatus control processing advances to step S108. If it is determined that the scan should be performed, the observation apparatus control processing advances to step S107. In step S106, the execution of the scan is determined under various conditions, for example, where the measurement by the measurement system is performed for the first time, where the user designates execution of the scan, where the current time is immediately before the start of repeatedly-executed measurement or determined based on time intervals set by the user, and where the user wishes to measure the entire region of the sample 300 in a wide range.

Figure 9:
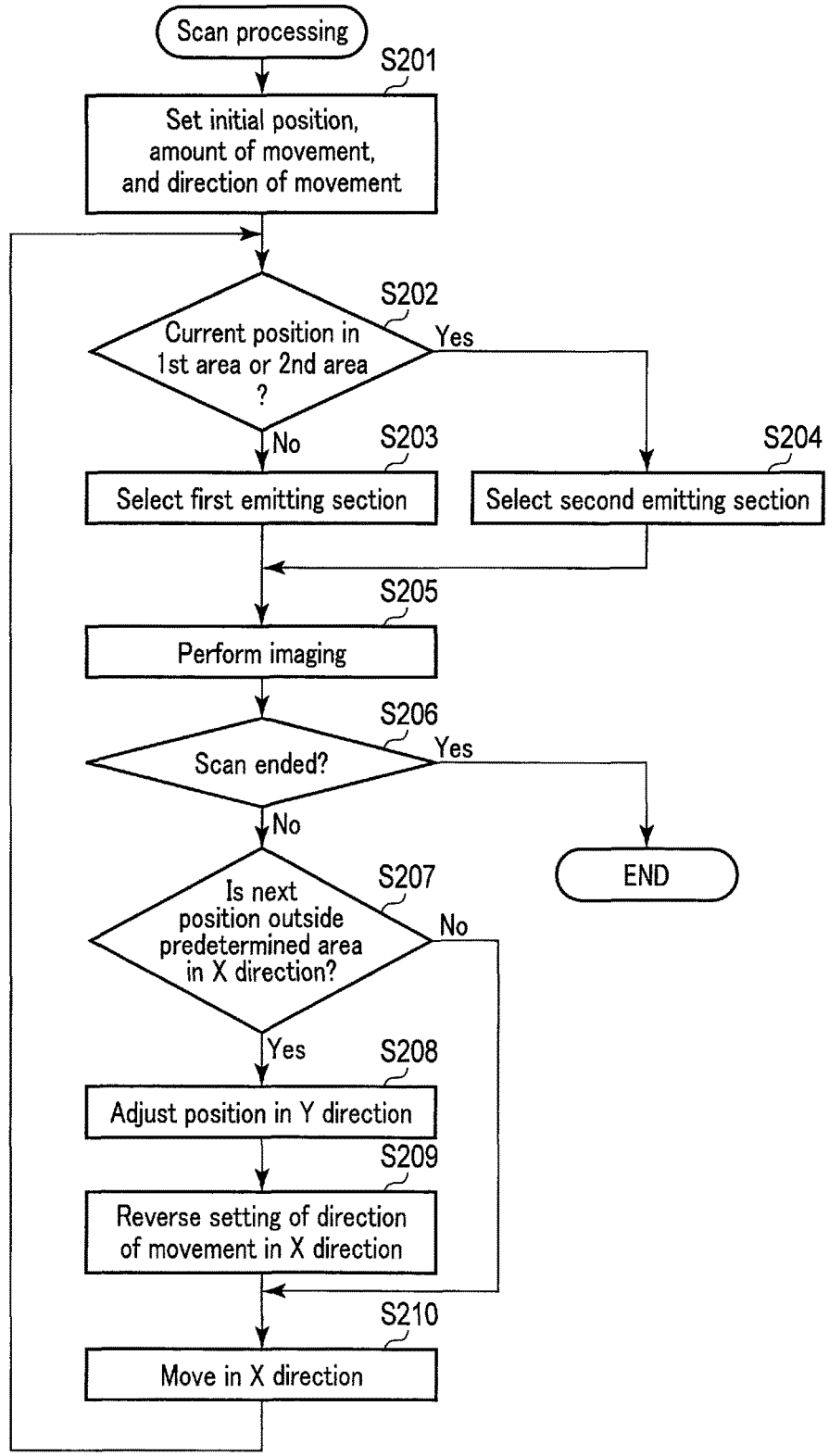
FIG. 9 is a flowchart illustrating an example of scan processing according to the first embodiment.

In step S107, the first control section 110 performs scan processing. FIG. 9 is a flowchart illustrating an example of scan processing according to the first embodiment. The scan processing will be described with reference to FIG. 9. In the scan processing, the first control section 110 performs illumination control based on the observation target range R0 and the position information on the imaging unit 120, so that the imaging can be performed under appropriate illumination control.

In step S201, the first control section 110 controls operations of the driving mechanism 160 so that the imaging unit 120 moves to the initial position. In the following, explanations are given on the assumption that the initial position is the center of the vessel 310; however, the initial position is not limited to the center of the vessel 310. For example, the initial position may be an edge portion of the vessel 310. The initial position may be set by inputting coordinate data by the user, or may be set by acquiring an image by preliminary scanning and then analyzing the image. The first control section 110 acquires the amounts of movement in the X and Y directions and the direction of movement during scanning based on outputs from the controller 200 in accordance with an input by the user or a value set in advance and stored in the first storage section 130. After the initial setting described above, the scan processing advances to step S202.

In step S202, the first control section 110 determines whether the position of the imaging unit 120 is inside the first area R1 or the second area R2 based on, for example, coordinate data indicating the position of the imaging unit 120 acquired by the first control section 110. As described above with reference to FIG. 8, the position of the vessel 310, that is, the observation target range R0, has already been acquired before the scan processing. Therefore, the included coordinates of each divided area are known, as described above with reference to FIG. 6. If the first control section 110 determines that the imaging unit 120 is not located in the first area R1 or the second area R2, the scan processing advances to step S203. If the imaging unit 120 is determined to be located in the first area R1 or the second area R2, the scan processing advances to step S204.

In each of step S203 and step S204, the first control section 110 selects an emitting section that emits the illumination light. The first control section 110 selects, as the emitting section that emits the illumination light, the first emitting section 183a in step S203 and the second emitting section 183b in step S204. In illumination switching in step S203 and step S204, an emitting section located inside the observation target range R0 is preferentially selected based on position information on the imaging unit 120 and the observation target range R0. Specifically, when the imaging unit 120 is located inside the first area R1 or the second area R2, the second emitting section 183b is selected, and when it is located outside the first area R1 and the second area R2, the first emitting section 183a is selected. After step S203 or step S204, the scan processing advances to step S205.

In step S205, the first control section 110 causes the emitting section selected in step S203 or step S204 to emit the illumination light and causes the imaging section 170 to perform imaging. At that time, the first control section 110 acquires a current position of the imaging unit 120. The first control section 110 also stores image data obtained by the imaging in the first storage section 130 or the second storage section 230. After the imaging, the scan processing advances to step S206.

In step S206, the first control section 110 determines whether or not the scan processing should be ended. For example, the position to end the scan processing is determined in advance based on the scan range, that is, the observation target range R0, a movement pattern of scan operations, etc. The movement pattern of scan operations is stored in the first storage section 130 or the second storage section 230 along with the vessel type information. The scanning range and the movement pattern of scan operations may be set by the user. If it is determined that the scan processing should not be ended, the scan processing advances to step S207.

In step S207, the first control section 110 determines whether or not the imaging unit 120 is located outside the observation target range R0 after next movement of the imaging unit 120 in the X direction. The determination is based on the current position of the imaging unit 120 acquired in the imaging in step S205, setting of the amount of movement, the preset movement pattern of the scan operations, etc. If it is determined that the imaging unit 120 is located outside the observation target range R0 after the movement, the scan processing advances to step S208. If not, that is, if it is determined that the imaging unit 120 is still located in the observation target range R0, the processing advances to step S210.

In step S208, the first control section 110 causes the driving mechanism 160 to move the imaging unit 120 in the Y direction by a predetermined amount. The amount of movement is based on the setting in step S201. Subsequently, the scan processing advances to step S209. In step S209, the first control section 110 reverses the setting of the direction of movement in the X direction. For example, if the direction of movement of the imaging unit 120 immediately before this step is the X+ direction, the first control section 110 switches the direction of movement to the X− direction. Subsequently, the scan processing advances to step S210.

In step S210, the first control section 110 causes the driving mechanism 160 to move the imaging unit 120 in the X direction by a predetermined amount. Subsequently, the first control section 110 continues repeating the processing from step S202 to step S210, until the scan processing is determined to be ended in step S206. If it is determined in step S206 that the repeated processing should be ended, the scan processing is ended and the processing advances to step S108 of the observation apparatus control processing.

Referring back to FIG. 7, the observation apparatus control processing after the completion of the scan processing will be described. In step S108, the first control section 110 determines whether or not manual position designation is performed. In other words, it is determined whether an imaging instruction is received from the controller 200 with designation of an imaging position. For example, the user can designate a position based on the image of the entire sample 300 obtained by the scan processing. The user can also designate an imaging position based on an image previously obtained by imaging in connection with measurement, instead of the images obtained by the scan processing. Unless an imaging instruction designating an imaging position is received, the observation apparatus control processing advances to step S110. If an imaging instruction is received, the observation apparatus control processing advances to step S109.

In step S109, the first control section 110 causes the driving mechanism 160 to move the imaging section 170 to a designated position and causes the imaging section 170 to acquire an image at that position. At this time, the first control section 110 performs illumination control as well as the scan processing. The first control section 110 transmits the acquired image to the controller 200 by way of the first communication device 192. Subsequently, the observation apparatus control processing advances to step S110.

In step S110, the first control section 110 determines whether or not the current time is a time when the measurement should be started. Unless the current time is a measurement start time, the processing advances to step S112. If the current time is a measurement start time, the processing advances to step S111. The measurement start time may be predetermined, for example, at the intervals of one hour. The measurement start condition need not depend on time but may depend on the state of the cell 324 or culture medium 322. In the present embodiment, measurement is repeatedly performed whenever the measurement start time comes.

In step S111, the first control section 110 performs measurement processing. In the measurement processing, the first control section 110 causes the imaging section 170 to repeat imaging under the illumination control of this embodiment described above with reference to FIG. 9. The first control section 110 performs predetermined processing for the acquired image data and records a requested result in the first storage section 130. Subsequently, the processing advances to step S112.

The range of movement of the imaging section 170 by the driving mechanism 160 in the measurement processing is, for example, the observation target range R0. The range of movement may be set by the user, for example, in step S108, step S109, etc. The range imaged by the measurement processing is, for example, a range in which cells of interest, such as a cell colony, are specified as being located, at the start of measurement. Alternatively, the range imaged by the measurement processing is a range in which the occurrence of a noteworthy change in a cell or the like is indicated by the imaging performed a number of times.

In the above description, a still image is taken in the scan processing, but this is not restrictive. Both in the scan processing and the measurement processing, still images may be taken for the respective position coordinates of the imaging section 170, and analysis may be performed based on the still images. Instead, moving images may be captured.

Figure 10:
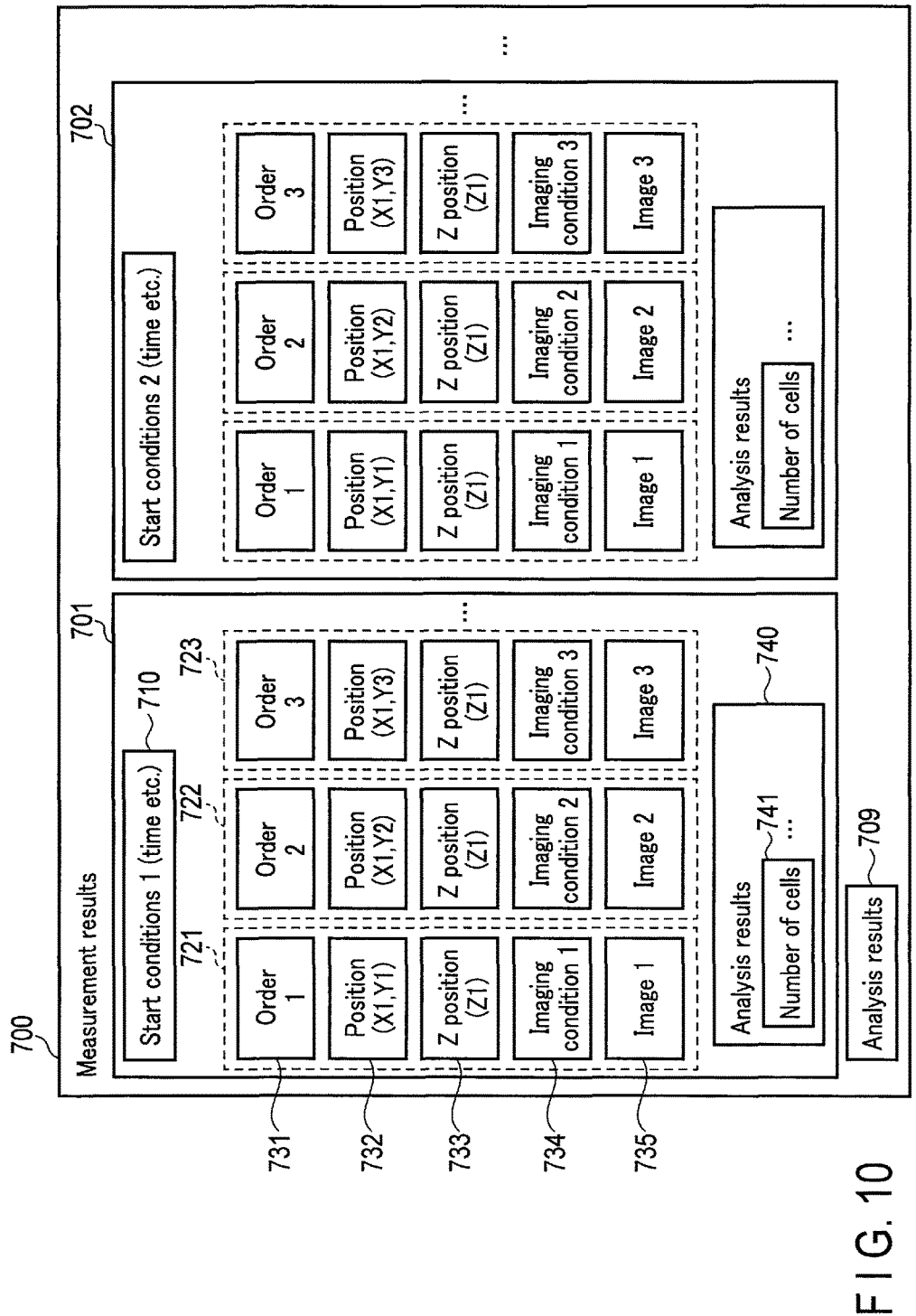
FIG. 10 is a diagram illustrating an outline of a configuration example of data of measurement results obtained by the measurement system according to the first embodiment.

Image acquisition performed in the measurement processing has been described with reference to FIG. 4. An example of a data structure of measurement results obtained as above and stored in the first storage section 130 is shown in FIG. 10. As shown in FIG. 10, measurement results 700 include first data 701 obtained by a first-time measurement, second data 702 obtained by a second-time measurement, etc. The number of data items increases or decreases in accordance with the number of times measurement is performed.

The first data 701 will be described by way of example. The first data 701 includes a start condition 710. This start condition 710 includes a condition under which the measurement start is determined in step S110. For example, a measurement start time is predetermined, and when measurement is started at this measurement start time, the measurement start time is recorded as a start condition 710.

In the first data 701, first image information 721, second image information 722, third image information 723, etc. are recorded. Each of these data is a set of data acquired in one-time imaging. The first image information 721 will be described by way of example. The first image information 721 includes an order 731, a position 732, a Z position 733, an imaging condition 734, and an image 735. The order 731 is indicated by serial numbers which are assigned to the imaging operations performed for respective positions. The position 732 includes an X coordinate and a Y coordinate of an imaging position. The X coordinate and the Y coordinate are values used in the control of the driving mechanism 160 and may be acquired by the position control section 111, for example. The Z position 733 includes a Z coordinate of an imaging position. The Z coordinate is a value used in the control of the imaging optical system 172 and may be acquired by the imaging control section 112, for example. The imaging condition 734 includes exposure conditions, such as a shutter speed and an aperture value, and other imaging conditions. The imaging conditions may differ, depending upon each imaging operation, they may be the same for the imaging operations included in the first data 701, or they may be the same for all imaging operations included in the measurement results 700. The image 735 is image data obtained by the imaging. Likewise, each of the second image information 722 and the third image information 723 includes information regarding an order, a position, a Z position, an imaging condition and an image. Where an imaging plane is not moved in the Z direction, the information on the Z position may be omitted.

The first data 701 includes analysis results 740. The analysis results 740 include a cell number 741 representing the number of cells or cell groups measured by the image processing circuit 140. The analysis results 740 may also include a plane image obtained by synthesizing the images of the same Z position. The analysis results 740 may also include a three-dimensional image obtained by synthesizing all images 735. The analysis results 740 may include a depth-synthesis image.

Like the first data 701, the second data 702 may include a start condition, first image data, second image data, third image data, analysis results, etc.

The measurement results 700 can include analysis results 709 of all measurements that are obtained based on the first data, second data, etc. All measurement results 700 may be recorded in one file; alternatively, part of the measurement results 700 may be recorded in one file.

Returning to FIG. 7, the description will be continued. In step S112, the first control section 110 determines whether or not a request for information is made by the controller 200. For example, the data obtained in step S111 is requested by the controller 200. Unless the request for information is made, the processing advances to step S114. If the request for information is made, the processing advances to step S113.

In step S113, the first control section 110 transmits the information requested by the controller 200 to the controller 200 through the first communication device 192. Subsequently, the processing advances to step S114.

In step S114, the first control section 110 determines whether or not the observation apparatus control processing should be ended. If it is determined that the observation apparatus control processing should be ended, the observation apparatus control processing is brought to an end. For example, when a series of measurements are ended and the observation apparatus 100 is removed from the incubator, the observation apparatus control processing is brought to an end. Unless the observation apparatus control processing is brought to an end, the processing advances to step S115.

In step S115, the first control section 110 determines whether or not the power source should be turned off. For example, if the standby time, which is from the measurement in step S111 to the next measurement, is long, the first control section 110 determines that the power source should be turned off to suppress the power consumption. Unless the power source is turned off, the processing returns to step S104. If it is determined that the power source should be turned off, the processing advances to step S116.

In step S116, the first control section 110 turns off each portion of the observation apparatus 100. Subsequently, the processing returns to step S101. In the above manner, the observation apparatus 100 repeatedly performs measurement.

Figure 11B:
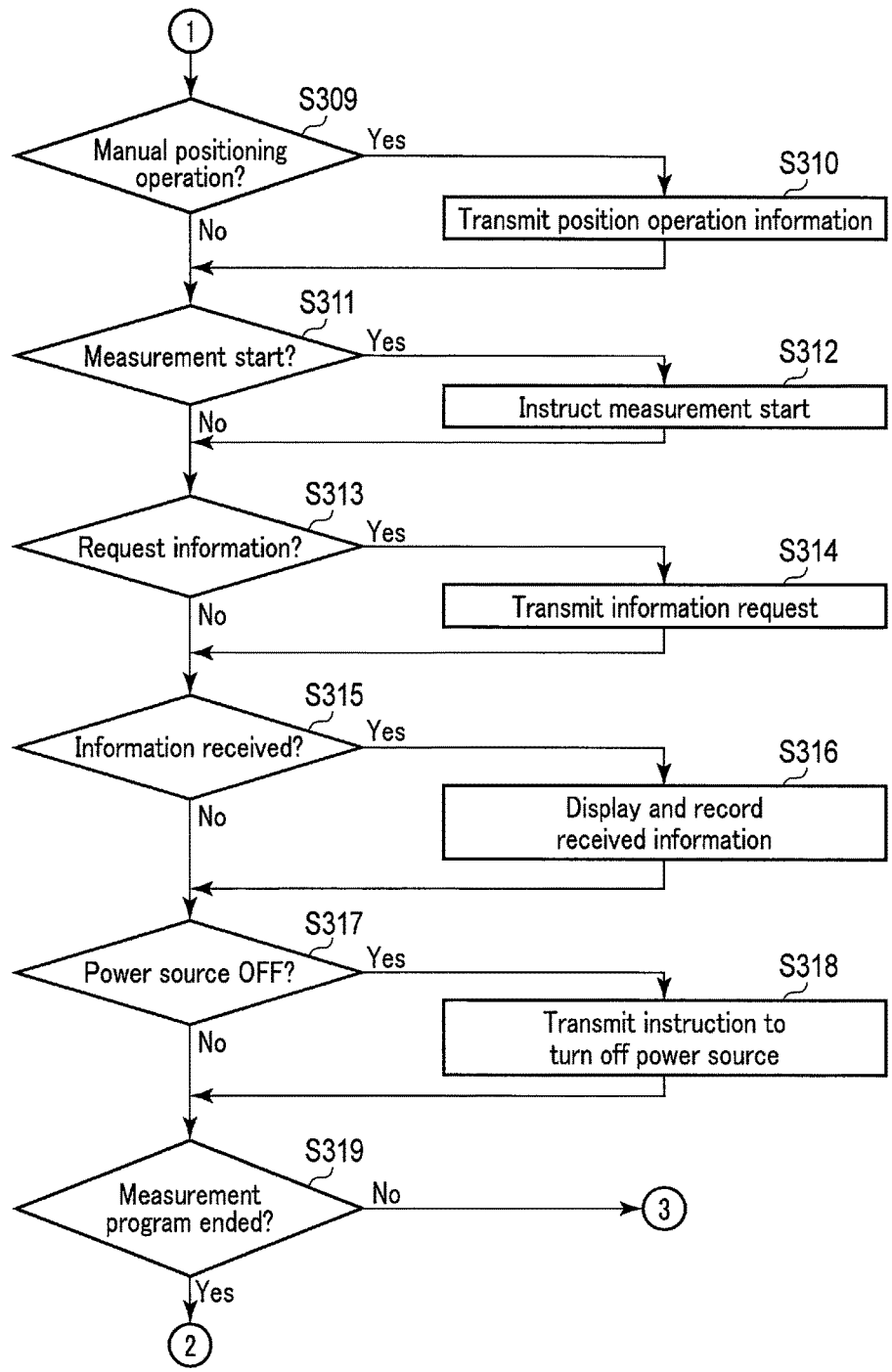
FIG. 11B is a flowchart illustrating an example of processing performed by a controller according to the first embodiment.

An example of control processing performed by the controller of the first embodiment will be described with reference to the flowcharts of FIG. 11A and FIG. 11B. The operations of the controller 200 will be explained with reference to FIG. 11A and FIG. 11B. The control processing performed by the controller starts after the observation apparatus 100, the controller 200, and the sample 300 are set in place.

In step S301, the second control section 210 determines whether or not a measurement program according to the present embodiment is activated. Unless the measurement program is activated, the processing of step S301 is repeated. The controller 200 is not limited to the functions of the controller of the measurement system of the present embodiment but may have various functions. Therefore, when the measurement program is not activated, the controller 200 may operate as a system other than the measurement system 1. If it is determined that the measurement program is activated, the processing advances to step S302.

In step S302, the second control section 210 establishes communications with the observation apparatus 100. This operation is related to step S103 of the observation apparatus control performed by the observation apparatus 100; that is, the observation apparatus 100 and the controller 200 operate so that communications between them are established. Subsequently, the processing performed by the controller advances to step S303. The communications established then may be low-power-consumption communications that is irrelevant to step S103 of the observation apparatus control and that only enables the transmission of an instruction to turn on the observation apparatus 100.

In step S303, the second control section 210 determines whether or not the user is requesting that the power source of the observation apparatus 100 be turned on. For example, if an instruction to turn on the observation apparatus 100 is supplied from the input device 274, the second control section 210 determines that the user is requesting that the power source be turned on. Unless the instruction to turn on the power source is supplied, the processing advances to step S305. If the instruction to turn on the power source is supplied, the processing advances to step S304. In step S304, the second control section 210 transmits to the observation apparatus 100 an instruction to turn on the power source of the observation apparatus 100. Subsequently, the processing advances to step S305. This operation is related to step S101 of the observation apparatus control performed by the observation apparatus 100. In the observation apparatus 100 which receives the instruction from the controller 200 to turn on the power source, the power source is turned on by the processing in step S102. The communication means used in the embodiment may be low-power-consumption communications such as Bluetooth Low Energy.

In step S305, the second control section 210 determines whether or not the user is requesting transmission of information to the observation apparatus 100. For example, if an instruction to transmit information is supplied from the input device 274, the second control section 210 determines that the user is requesting transmission of information. The information the transmission of which is requested is information on a vessel type, measurement conditions, etc. Unless the transmission of information is requested, the processing advances to step S307. If the transmission of information is requested, the processing advances to step S306. In step S306, the second control section 210 transmits the information entered from the input device 274 to the observation apparatus 100. Subsequently, the processing advances to step S307. This operation is related to step S104 of the observation apparatus control performed by the observation apparatus 100. The observation apparatus 100 acquires the information transmitted from the controller 200 to the observation apparatus 100 in step S105.

In step S307, the second control section 210 determines whether or not the user is requesting that the observation apparatus 100 perform scan processing. For example, if an instruction related to execution of the scan processing is supplied from the input device 274, the second control section 210 determines that the user is requesting execution of the scan processing. Unless the scan processing is requested, the processing advances to step S309. If the scan processing is requested, the processing advances to step S308. In step S308, the second control section 210 transmits an instruction to start the scan processing to the observation apparatus 100. Subsequently, the processing advances to step S309. This operation is related to step S106 of the observation apparatus control performed by the observation apparatus 100. The observation apparatus 100 performs scan processing in step S107, based on the scan processing start instruction transmitted from the controller 200 to the observation apparatus 100.

In step S309, the second control section 210 determines whether or not the user manually designates a position to be imaged by the observation apparatus 100. For example, if an imaging position is entered from the input device 274, the second control section 210 determines that an imaging position has been designated. Unless the imaging position is designated, the processing advances to step S311. If the imaging position is designated, the processing advances to step S310. In step S310, the second control section 210 transmits the imaging position entered from the input device 274 to the observation apparatus 100. Subsequently, the processing advances to step S311. This operation is related to step S108 of the observation apparatus control performed by the observation apparatus 100. Position adjustment is made in step S109 in accordance with the imaging position transmitted from the controller 200 to the observation apparatus 100. An image is acquired at that position and transmitted.

In step S311, the second control section 210 determines whether or not the user is requesting that the observation apparatus 100 start measurement. For example, if an instruction to start measurement by the observation apparatus 100 is supplied from the input device 274, the second control section 210 determines that the user is requesting the start of measurement. If the start of measurement is not requested, the processing advances to step S313. If the start of measurement is requested, the processing advances to step S312. In step S312, the second control section 210 transmits an instruction to start measurement to the observation apparatus 100. Subsequently, the processing advances to step S313. This operation is related to step S110 of the observation apparatus control performed by the observation apparatus 100. Measurement is performed in step S111 in accordance with the instruction transmitted from the controller 200 to the observation apparatus 100.

In step S313, the second control section 210 determines whether or not the user is requesting acquiring information from the observation apparatus 100. For example, if an instruction to request information is supplied from the input device 274, the second control section 210 determines that the user is requesting information. The information requested then is, for example, information on the sample 300 obtained by the observation apparatus 100. The information can be information contained in the measurement results 700 described with reference to FIG. 10, including image data on the sample 300 and the number of cells or cell groups in the sample 300. Unless the information is requested, the processing advances to step S315. If the information is requested, the processing advances to step S314. In step S314, the second control section 210 transmits an instruction to transmit the user's requested information to the observation apparatus 100. Subsequently, the processing advances to step S315. This operation is related to step S112 of the observation apparatus control performed by the observation apparatus 100. The information requested in step S113 is transmitted from the observation apparatus 100 to the controller 200 in accordance with the information request transmitted from the controller 200 to the observation apparatus 100.

In step S315, the second control section 210 determines whether or not the information requested in step S314 is received. Unless the information is received, the processing advances to step S317. If the information is received, the processing advances to step S316. In step S316, the second control section 210 displays the received information on the display 272 or records it in the second storage section 230. Subsequently, the processing advances to step S317.

In step S317, the second control section 210 determines whether or not the user is requesting that the power source of the observation apparatus 100 be turned off. For example, if an instruction to turn off the power source of the observation apparatus 100 is supplied from the input device 274, the second control section 210 determines that the user is requesting that the power source be turned off. Unless the instruction to turn off the power source is supplied, the processing advances to step S319. If the instruction to turn off the power source is supplied, the processing advances to step S318. In step S318, the second control section 210 transmits to the observation apparatus 100 an instruction to turn off the power source of the observation apparatus 100. Subsequently, the processing advances to step S319. This operation is related to step S115 of the observation apparatus control performed by the observation apparatus 100. The power source is turned off in step S116 in accordance with the turn-off instruction transmitted from the controller 200 to the observation apparatus 100.

In step S319, the second control section 210 determines whether or not the measurement program comes to an end. If the measurement program ends, the processing returns to step S301. Unless the measurement program ends, the processing returns to step S303. Thus, the above operation is repeatedly executed.

As described above, the measurement by the measurement system 1 can be repeatedly performed at predetermined timings and under predetermined conditions. Measurement timings and measurement conditions may be entered by the user from the controller 200 and set in the observation apparatus 100. The measurement by the measurement system 1 may be manually performed based on a user's instruction when the instruction to start the measurement is entered by the user from the controller 200 and is supplied to the observation apparatus 100.

<Advantage of the Measurement System>

The first control section 110 acquires position information on the imaging unit 120 moved by the driving mechanism 160, and the observation target range R0, that is, position information on the vessel 310. The first control section 110 determines which region of the areas of the observation target range R0 the current position of the imaging unit 120 corresponds to, based on the acquired position information. The first control section 110 performs illumination control, such as selecting an emitting section to emit illumination light in accordance with the area where the imaging unit 120 is located and switching between the emitting sections as needed to maintain an appropriate illumination environment. The measurement system 1 of this embodiment suppresses scattering of the illumination light at the vessel edge portion of the sample 300 under the illumination control and can acquire a quality image.

In the measurement system 1 of this embodiment, only the emitting section that emits necessary and sufficient illumination light can be used. Therefore, emission of unnecessary illumination light can be restricted as compared to a case where, for example, two emitting sections always emit illumination light or a light source, such as a ring light, always emits illumination light. Accordingly, the technique of this embodiment also contributes to saving of energy necessary for using the measurement system 1. Furthermore, due to the illumination control, unnecessary illumination need not be lit. Therefore, the measurement system 1 of this embodiment can reduce the amount of heat generation resulting from lighting of the illumination.

If there is another emitting section in the observation target range R0 in addition to the emitting section selected in accordance with the position information, the other emitting section may be off, or may emit a less amount of light as supplementary illumination.

In the example described above, the second emitting section 183b is selected when the imaging unit 120 is located in the first area R1 and the second area R2, and the first emitting section 183a is selected when the imaging unit 120 is located in the third area R3 and the fourth area R4 as a rule to select an emitting section; however, the embodiment is not limited to this example. In the illumination control of this embodiment, it is important that the illumination light emitted from the selected emitting section does not scatter at the vessel edge portion of the sample 300. Therefore, the rule to select an emitting section that emits illumination light may be anything as long as an emitting section located in the observation target range R0 can be selected as the emitting section that emits the illumination light.

Second Embodiment

A second embodiment of the present invention will be explained below. In the following, matters different from the first embodiment will be explained. Identical symbols will be used for identical parts, and detailed explanations thereof will be omitted. FIG. 12 shows an outline of a configuration example of an imaging unit according to the second embodiment. In the first embodiment, the first control section 110 selects which of the two emitting sections should emit illumination light. In contrast, in the second embodiment, an imaging unit 120 shown in FIG. 12 further comprises a third emitting section 183c and a fourth emitting section 183d in addition to the first emitting section 183a and the second emitting section 183b. Accordingly, the illumination optical system 182 may further comprise a third illumination optical system and a fourth illumination optical system, and the light source 184 may further comprise a third light source and a fourth light source. As well as the first embodiment, each of the emitting sections may be included in any portion of the illumination section 180. In this embodiment, the first control section 110 selects which of the four emitting sections should emit illumination light.

Referring to FIG. 12, an example of the configuration of the imaging unit 120 of this embodiment will be explained in detail. The emitting sections are arranged almost symmetrically with respect to the imaging section 170 or the imaging optical system 172. In other words, the imaging section 170 or the imaging optical system 172 is arranged between the emitting sections. A line segment connecting the position of the third emitting section 183c and the position of the fourth emitting section 183d is almost perpendicular to a line segment connecting the position of the first emitting section 183a and the position of the second emitting section 183b. For example, the first emitting section 183a is provided on a side of the X− direction of the imaging optical system 172, the second emitting section 183b is provided on a side of the X+ direction of the imaging optical system 172, the third emitting section 183c is provided on a side of the Y− direction of the imaging optical system 172, and the fourth emitting section 183d is provided on a side of the Y+ direction of the imaging optical system 172. The configuration of the imaging unit 120 is not limited to the example described above. Arrangement of the elements of the imaging unit 120 in the X-axis direction and the Y-axis direction is not limited to the example described above. For example, the second emitting section 183b and the fourth emitting section 183d may be arranged in the X-axis direction. Alternatively, an arrangement in which the configuration shown in FIG. 12 is rotated on the same plane may be employed.

An observation target range R0 of this embodiment is the same as the example of the first embodiment described with reference to FIG. 6. In the description of this embodiment, explanations will be given about how the first control section 110 performs illumination controls in each of the divided areas in a case where the imaging unit 120 has a configuration as shown in FIG. 12, and the observation target range R0 is divided into the areas as shown in FIG. 6. In the following explanations, in illumination A, the first emitting section 183a emits illumination light. Similarly, in illumination B, illumination C, and illumination D, the second emitting section 183b, the third emitting section 183c and the fourth emitting section 183d respectively emit illumination light. In the illumination control of this embodiment, as described above for the first embodiment with reference to FIG. 5, an illumination within the observation target range R0 can be selected in accordance with the position information on the imaging unit 120 and the observation target range R0.

In this embodiment, possible combinations of illuminations that can be selected in each of the divided areas are as follows: When the imaging unit 120 is located in the first area R1, the first control section 110 selects the illumination B or the illumination C. When the imaging unit 120 is located in the second area R2, the first control section 110 selects the illumination B or the illumination D. When the imaging unit 120 is located in the third area R3, the first control section 110 selects the illumination A or the illumination D. When the imaging unit 120 is located in the fourth area R4, the first control section 110 selects the illumination A or the illumination C. Thus, in this embodiment, two of the illuminations can be selected as candidates for a main illumination.

Under the illumination control of this embodiment, the two illuminations selected as the candidates for the main illumination may be simultaneously turned on, or either one of the two may be selectively turned on. The illuminations other than those selected as the candidates for the main illumination may, for example, emit a reduced amount of illumination light, or may be turned off.

The second embodiment can produce the same effect as the first embodiment. In comparison with the first embodiment, more appropriate illumination control can be executed, since the second embodiment includes a greater number of illuminations that can be supplementarily used.

Third Embodiment

A third embodiment of the present invention will be explained below. In the following, matters different from the first or second embodiment will be explained. Identical symbols will be used for identical parts, and detailed explanations thereof will be omitted. In the first embodiment, the imaging unit 120 includes two illuminations and the first control section 110 selects which of the two should emit illumination light. In contrast, according to this embodiment, the imaging unit 120 includes the four illuminations A to D, as described above for the second embodiment with reference to FIG. 12. The first control section 110 selects which of the four illuminations should emit illumination light. In this embodiment, the number of the divided areas of the observation target range R0 is four as well as the second embodiment; however, the manner of division is different from that of the second embodiment.

FIG. 13 is a diagram illustrating an example of an observation target range R0 and a manner of division of the same in the illumination control according to the third embodiment. In this embodiment, the observation target range R0 is divided into four areas as shown in FIG. 13 to perform illumination control. The divided areas are hereinafter referred to as a fifth area R5, a sixth area R6, a seventh area R7, and an eighth area R8.

The observation target range R0 is divided into three in the Y direction, and the central area of the three is divided into two in the X direction. Of the two divided areas in the X direction, the area of a side in the X− direction is the fifth area R5, and the area of a side in the X+ direction is the sixth area R6. Of the three divided areas in the Y direction of the observation target range R0, the part that is other than the central area and on a side in the Y+ direction is the seventh area R7. The area other than the fifth area R5 to the seventh area R7 of the observation target range R0, namely, the part that is other than the central area of the three divided areas in the Y direction and on a side in the Y− direction, is the eighth area R8.

Figure 14:
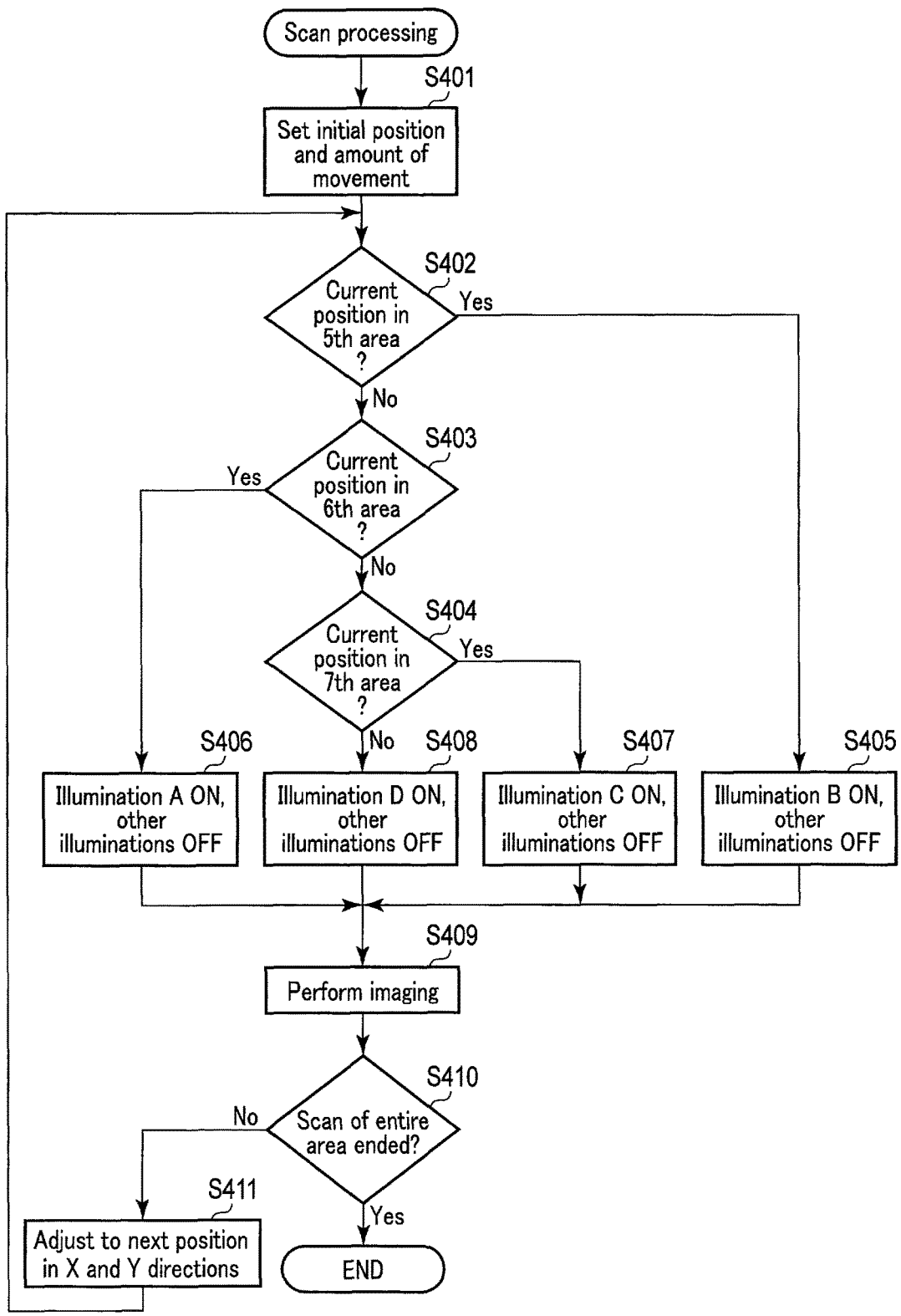
FIG. 14 is a flowchart illustrating an example of scan processing according to the third embodiment.

FIG. 14 is a flowchart illustrating an example of scan processing according to the third embodiment. Scan processing in this embodiment includes illumination control based on a position of the imaging unit 120 in the Y direction in addition to the scan processing in the first embodiment carried out based on a relative position between each of the four divided areas and the imaging unit 120. The configuration of the imaging unit 120 is the same as that in the second embodiment.

In step S401, the first control section 110 sets an initial position and amounts of movement in the X direction and the Y direction in the same manner as in step S201 of the scan processing of the first embodiment. The initial position may be the center of the observation target range R0 or any other position. The observation target range R0 varies depending on the type of the vessel 310. The vessel type information relating to the vessel 310 to be used is acquired before the scan processing is executed; therefore, the shape, the size, and the position of the vessel are known.

In step S402 to step S404, the first control section 110 determines a current position of the imaging unit 120 in the same manner as in step S202 of the scan processing of the first embodiment. If the current position of the imaging unit 120 is determined to be in the fifth area R5 in step S402, the scan processing advances to step S405. If the current position of the imaging unit 120 is determined to not be in the fifth area R5, the scan processing advances to step S403. If the current position of the imaging unit 120 is determined to be in the sixth area R6 in step S403, the scan processing advances to step S406. If the current position of the imaging unit 120 is determined to not be in the sixth area R6, the scan processing advances to step S404. If the current position of the imaging unit 120 is determined to be in the seventh area R7 in step S404, the scan processing advances to step S407. If the current position of the imaging unit 120 is determined to not be in the seventh area R7, the scan processing advances to step S408.

In step S405, the first control section 110 selects the illumination B as the illumination that emits illumination light based on the determination that the imaging unit 120 is in the fifth area R5. In step S406, the first control section 110 selects the illumination A as the illumination that emits illumination light based on the determination that the imaging unit 120 is in the sixth area R6. In step S407, the first control section 110 selects the illumination C as the illumination that emits illumination light based on the determination that the imaging unit 120 is in the seventh area R7. In step S408, the first control section 110 selects the illumination D based on the determination that the imaging unit 120 is in the area other than the fifth area R5 to the seventh area R7 of the observation target range R0, namely, in the eighth area R8. After each of step S405 to step S408, the scan processing advances to step S409.

In step S409, the first control section 110 causes the imaging section 170 to perform imaging in the same manner as in step S205 of the scan processing of the first embodiment. After the imaging, the scan processing advances to step S410. In step 410, the first control section 110 determines whether or not the scanning of the entire observation target range R0 is ended in the same manner as in step S206 of the scan processing of the first embodiment. If it is determined that the scan processing is not ended, the scan processing advances to step S411.

In step S411, the first control section 110 causes the driving mechanism 160 to move the imaging unit 120 in the X direction and the Y direction by a predetermined amount. The amounts of movement in the X direction and the Y direction are determined based on the setting in S401. Movement patterns of scan operations, such as the order of movements in the X direction and the Y direction, are stored in the first storage section 130 or the second storage section 230 together with the vessel type information. The movement patterns of scan operations may be set in step S401. Subsequently, the scan processing returns to step S402.

After returning to step S402, the first control section 110 continues repeating the processing from step S402 to step S411, until the observation target range R0 or a preset area is entirely scanned. If it is determined in step S410 that the repeated processing should be ended, the scan processing is ended and the processing advances to step S108 of the observation apparatus control processing. In this embodiment, the number of illuminations that are turned on is not limited to one, as described above in connection with the first embodiment. For example, the expression "other illuminations OFF" in FIG. 14 means merely that the other, non-selected illuminations are not a main illumination.

The third embodiment can produce the same effect as the first embodiment. In comparison with the first embodiment, more appropriate illumination control can be executed, since the technique of this embodiment additionally includes illumination control based on a position of a vessel edge portion in the Y direction and a greater number of emitting sections that can be supplementarily used. Furthermore, the technique of this embodiment is described as an example in which the observation target range R0 is divided in the manner of division different from that of the second embodiment. Thus, since the technique of this embodiment can execute appropriate illumination control without an interference with imaging by a vessel edge portion, the scanning method is not specifically limited.

Fourth Embodiment

The technique relating to the illumination control as described above selects a candidate for an illumination based on position information on the sample 300 and the imaging unit 120, and switches between the illuminations. In this embodiment, a plurality of illuminations are selected as candidates for illuminations depending on a position where the imaging unit 120 is located, and an illumination to be turned on is further selected in the manner described below. In this embodiment, divided areas of the observation target range R0 are those explained above with reference to FIG. 6. The imaging unit 120 has a configuration as explained above with reference to FIG. 12. As previously explained, the selected illumination is an illumination that mainly lights. The other, non-selected illuminations may be turned off or supplementarily lit with a reduced amount of light.

Figure 15:
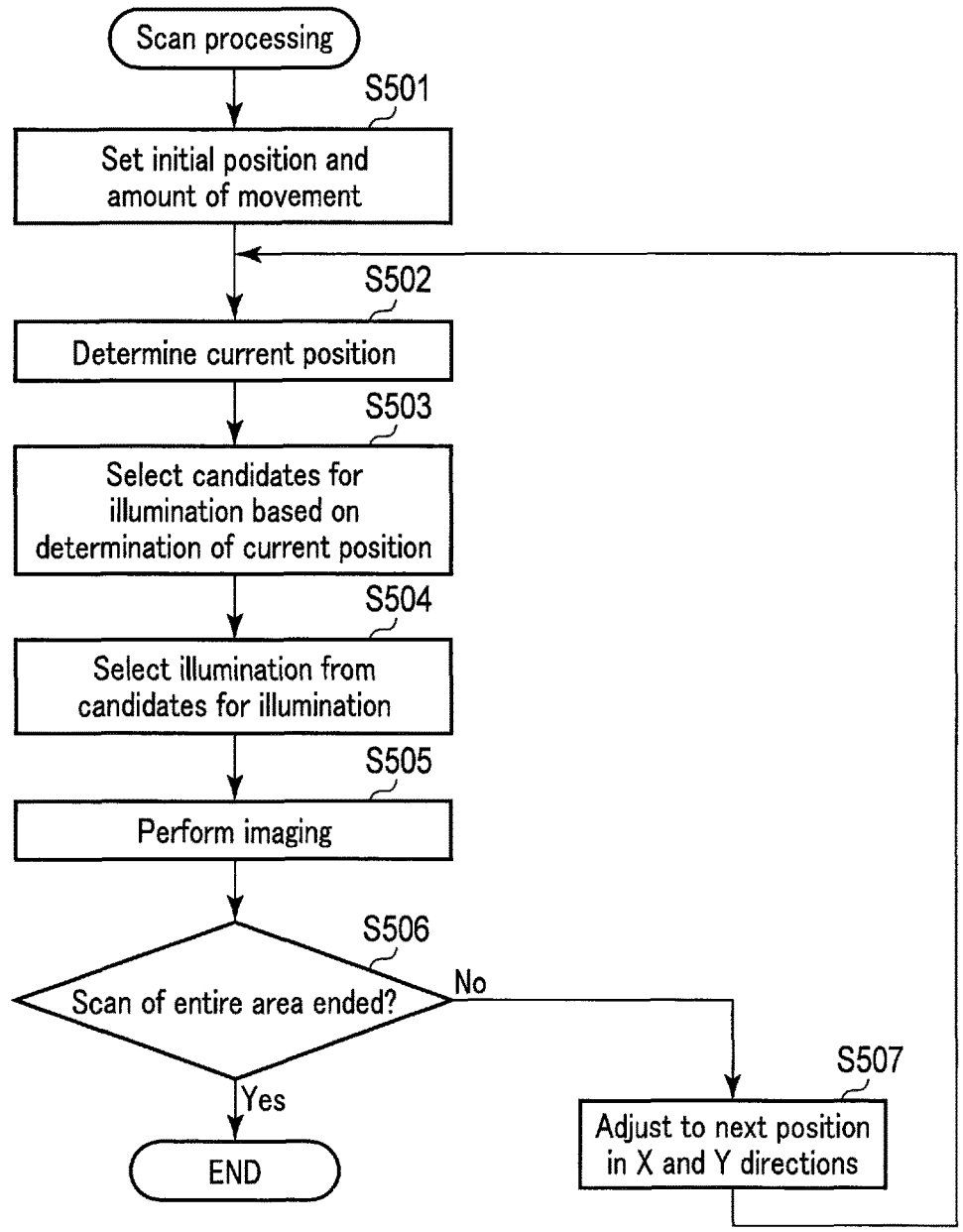
FIG. 15 is a flowchart illustrating an example of scan processing according to a fourth embodiment.

FIG. 15 is a flowchart illustrating an example of scan processing according to the fourth embodiment. In the following, explanations of the scan processing of the fourth embodiment will be given in comparison with processing in each step of the scan processing of the third embodiment described with reference to FIG. 14.

In step S501, the first control section 110 sets the initial position and the amount of movement in the same manner as in step S401. Subsequently, the scan processing advances to step S502.

In step S502, the first control section 110 determines in which of the first area R1 to the fourth area R4 the current position of the imaging unit 120 is, in the same manner as in step S402 to step S404. Subsequently, the scan processing advances to step S503.

In step S503, the first control section 110 selects a candidate for an illumination based on the position information on the observation target range R0 and the imaging unit 120, in the same manner as in step S405 to step S408. An illumination selected as a candidate for the illumination in each of the divided areas, namely, the first area R1 to the fourth area R4, is the same as that described above in connection with the second embodiment. When the imaging unit 120 is located in the first area R1, the illumination B or the illumination C is selected. When the imaging unit 120 is located in the second area R2, the illumination B or the illumination D is selected. When the imaging unit 120 is located in the third area R3, the illumination A or the illumination D is selected. When the imaging unit 120 is located in the fourth area R4, the illumination A or the illumination C is selected.

In step S504, the first control section 110 further selects an illumination to be lit from the candidates for illuminations. In this embodiment, an illumination to be lit is selected on the basis of one or the combination of an accumulated lighting time period of each of the illuminations and a movement locus of the imaging unit 120. The accumulated lighting time period of the illumination may be equivalent to the accumulated lighting time period of the light source. Each of selections of the illuminations will be described later. Subsequently, the scan processing advances to step S505.

In step S505, the first control section 110 images the sample 300 in the same manner as in step S409. Subsequently, the scan processing advances to step S506. In step S506, the first control section 110 determines whether or not the scan processing should be ended in the same manner as in step S410. If it is determined that the scan processing should not be ended, the scan processing advances to step S507. In step S507, the first control section 110 moves the imaging unit 120 to a next imaging position in the same manner as in step S411. Subsequently, the first control section 110 continues repeating the scan processing from step S502 to step S507, until the scan processing is determined to be ended in step S506. If it is determined in step S506 that the scan processing should be ended, the repeated processing is ended and the processing advances to step S108 of the observation apparatus control processing.

(Selection of an Illumination Based on Accumulated Lighting Time Periods of the Respective Illuminations)

As the accumulated lighting time period of an LED increases, the LED gradually deteriorates, and the amount of light beams which can be emitted from the LED decreases; that is, the brightness is decreased. Therefore, for example, if LEDs are used as light sources, an illumination is selected on the basis of the accumulated lighting time period of each of the illuminations. Accordingly, the technique of this embodiment can obviate a situation in which the accumulated lighting time period of a part of the LEDs becomes exceedingly long and a considerable difference occurs in the amount of light emitted from the respective LEDs, and can maintain an appropriate illumination environment.

In this embodiment, the light source 184 of a shorter accumulated lighting time period has a higher lighting priority. FIG. 16 illustrates an example of lighting priorities of illuminations under illumination control based on the accumulated lighting time period of each of the illuminations. As shown in FIG. 16, for example, it is assumed that the illumination B, the illumination A, the illumination D, and the illumination C have higher lighting priorities in this order based on the accumulated lighting time periods.

For example, explanations will be given for a case in which the current position of the imaging unit 120 is determined to be in the third area R3 in step S502. In step S503, the first control section 110 selects the illumination A and the illumination D as switchable illuminations based on position information. In step S504, the first control section 110 compares the accumulated lighting time period of the illumination A and that of the illumination D, and selects and lights the illumination A having a higher lighting priority based on the accumulated lighting time periods. The accumulated lighting time periods are updated in accordance with lighting of the illuminations, and the lighting priorities are also updated accordingly, immediately before step S502, for example.

(Selection of an Illumination Based on a Movement Locus of the Imaging Unit)

When switching between illuminations, a state of an illumination changes depending on a variation specific to the light source, such as an LED, a position of the illumination, arrangement of the illuminations, etc. The influence of the change on the captured image can be suppressed to a certain extent by appropriate designing, but cannot be completely eliminated. In this embodiment, therefore, the switching between illuminations due to a movement of the imaging unit 120 is suppressed to a minimum.

FIG. 17 illustrates an example of illuminations selected under illumination control based on a movement locus of the imaging unit. In the figure, the illuminations indicated by a single circle or a double circle represent candidates for the illumination selected in step S503 and selectable in the area. The illumination indicated by the double circle represents an illumination to be lit selected in step S504. As shown in FIG. 17, for example, it is assumed that the imaging unit 120 moves from the first area R1, the fourth area R4, and the third area R3 to the second area R2 in this order. It is also assumed that the movement pattern of the imaging unit 120 is stored in advance in the first storage section 130 or the second storage section 230, as described above.

For example, the current position of the imaging unit 120 is in the first area R1, and the illumination C is lit. Explanations will be given for a case in which the imaging unit 120 is moved in step S507 and the current position of the imaging unit 120 is determined to be in the fourth area R4 in step S502. In step S503, the first control section 110 selects the illumination A and the illumination C as candidates for switchable illuminations, based on position information. In step S504, the first control section 110 selects the illumination C from the illumination A and the illumination C selected as the candidates for illuminations, so that the imaging can continue without changing the illuminations.

Then, the imaging unit 120 is moved. If the current position of the imaging unit 120 is determined to be in the third area R3 in step S502, the first control section 110 selects the illumination A and the illumination D as candidates for switchable illuminations in step S503 based on position information. The currently lit illumination C is not included in the candidates for illuminations. At this time, the first control section 110 refers to candidates for illuminations that can be selected based on position information in, for example, the area where the imaging unit 120 is going to be moved next. As described above, the order of movement of the imaging unit 120 is known; that is, the imaging unit 120 is moved to the second area R2 after the third area R3. In the second area R2, the candidates for illuminations that can be selected based on position information are the illumination B and the illumination D. Therefore, the first control section 110 selects the illumination D to avoid unnecessary switching of the illuminations. Furthermore, if the lit illumination is not included in the candidates for illuminations that can be selected as described above, priorities for selecting which of the candidates should be turned on may be set in advance, so that an illumination can be selected in accordance with the setting.

Thus, according to the technique of this embodiment, when the imaging unit 120 is moved into a different area, the illumination that is lit just before the movement is continuously selected as long as possible, or an illumination to be lit is selected with reference to next candidates for the illuminations, thereby decreasing the frequency of switching the illuminations. As a result, a change in exposure of the acquired image data can be reduced. Furthermore, during a moving picture recording or a live view observation, image flickering due to switching of the illuminations can be reduced. The live view observation is a function for imaging and displaying a moving picture for observation, but not recording the moving picture. Thus, the technique of this embodiment carries out illumination control corresponding to the position information on the observation target range R0 and the imaging unit 120 and performs illumination control based on histories of lighting the respective illuminations.

(Selection of an Illumination Based on Accumulated Lighting Time Periods of the Respective Illuminations and a Movement Locus of the Imaging Unit)

The selection of an illumination based on the accumulated lighting time periods of the respective illuminations may be used in combination with the selection of an illumination based on the movement locus of the imaging unit 120. FIG. 18 illustrates an example of illuminations selected in illumination control based on the accumulated lighting time period of each of the illuminations and the movement locus of the imaging unit 120. In the following explanations, the lighting priorities based on the accumulated lighting time periods are assumed to be the same as those described above with reference to FIG. 16 concerning the selection of illuminations based on the accumulated lighting time period of each illumination. The meanings of single circles and double circles in the figure and the order of movement of the imaging unit 120 are assumed to be the same as those described above in connection the selection of illuminations based on the movement locus of the imaging unit 120. In this embodiment, if the result of selection of an illumination based on accumulated lighting time periods of the respective illuminations is inconsistent with the result of selection of an illumination based on the movement locus of the imaging unit 120, preference is given to the selection that does not require switching of the illuminations, although there is an exception described below.

For example, assume that the current position of the imaging unit 120 is in the first area R1, and the illumination B is lit. In the case described below, the imaging unit 120 is moved in step S507, and the current position of the imaging unit 120 is determined to be in the fourth area R4 in step S502. In step S503, the first control section 110 selects the illumination A and the illumination C as candidates for the switchable illuminations based on the position information. Thus, since the illumination B currently lit is not included in the candidates for the switchable illuminations, the illumination is switched. The first control section 110 selects the illumination A, which has a higher lighting priority based on the accumulated lighting time periods.

Subsequently, the imaging unit 120 is moved. In step S502, if it is determined that the current position of the imaging unit 120 is in the third area R3, the first control section 110 still selects the illumination A as a result of selection of candidates for the illuminations based on the position information in step S503 and a result of selection of illuminations based on the movement locus in step S504.

Subsequently, if the current position of the imaging unit 120 is determined to be in the second area R2, the illumination B, which has a higher lighting priority, is selected as the illumination to be lit from the candidates for illuminations, namely, the illumination B and the illumination D. Subsequently, if the current position of the imaging unit 120 is determined to be in the first area R1, the illumination B, which has a higher lighting priority and does not need switching of the illuminations, is selected as the illumination to be lit from the candidates for illuminations, namely, the illumination B and the illumination C. Subsequently, at timing T1, if the current position of the imaging unit 120 is determined to be in the fourth area R4, the illumination A, which has a higher lighting priority, is selected as the illumination to be lit from the candidates for illuminations, namely, the illumination A and the illumination C.

For example, explanations will be given for a case in which the accumulated lighting time period of the illumination A becomes longer than the accumulated lighting time period of the illumination D by a predetermined period of time or longer at timing T1. The lighting priorities based on the accumulated lighting time periods are updated, for example, immediately before step S502.

At timing T2, the imaging unit 120 is in the third area R3. In step S503, the illumination A and the illumination D are selected as candidates for the illuminations. At this time, since the lighting priorities were updated at timing T1, the illumination D is selected, according to the selection of the illuminations based on the accumulated lighting time periods of the respective illuminations. On the other hand, according to the selection of the illuminations based on the movement locus of the imaging unit 120, the illumination A, which is lit just before, is selected so that the illuminations will not be switched.

As described above, in this embodiment, preference is given to the selection that does not require switching of the illuminations. However, if the difference between the accumulated lighting time periods exceeds a threshold, the first control section 110 gives preference to the selection based on the lighting priorities and switches the illuminations.

Even if the accumulated lighting time period of the illumination A becomes longer than the accumulated lighting time period of the illumination D, if the difference therebetween does not exceed a threshold, preference is given to the selection that does not require switching of the illuminations, as described above. As a result, the illumination A is selected. For example, as shown in FIG. 18, the current position of the imaging unit 120 is determined to be in the second area R2 after timing T2. Then, the illumination B and the illumination D are selected as candidates for illuminations. At this time, according to the selection of the illuminations based on the accumulated lighting time periods of the respective illuminations, the illumination B is selected. On the other hand, according to the selection of the illuminations based on the movement locus of the imaging unit 120, the illumination D, which is lit at timing T2, is selected so that the illuminations will not be switched. Here, as described above, preference is given to the selection that does not require switching of the illuminations, and the illumination D is selected instead of the illumination B having a higher lighting priority.

The illumination control based on the selection of the illuminations of this embodiment has advantages described below in addition to the advantages of the measurement system 1 obtained by the first to third embodiments. The light source 184, such as an LED, deteriorates as the accumulated lighting time period of the LED increases. Accordingly, for example, the brightness of the illumination light, which can be emitted from the LED, is decreased. The technique of this embodiment carries out illumination control so as not to produce a great difference between the accumulated lighting time periods of the respective illuminations. Thus, the technique of this embodiment can obviate a situation in which a great difference occurs in the amount of light emitted from the respective light sources 184, and can maintain an appropriate illumination environment. Furthermore, when switching between illuminations, the exposure changes depending on a variation specific to the light source 184, such as an LED, a position of the illumination, arrangement of the illumination, etc. The technique of this embodiment can avoid unnecessary switching of the illuminations based on the movement locus of the imaging unit 120. As a result, a change in exposure that occurs when switching between illuminations can be reduced.

<Modification>

(First Modification Relating to Acquisition of a Vessel Position)

In the embodiments described above, the position of the vessel 310, that is, the observation target range R0, is acquired based on the vessel type information registered in advance. However, the invention is not limited to the embodiments. For example, simple scan processing, namely rough scan processing, may be carried out before the scan processing so that the first control section 110 can acquire the vessel type, or the observation target range R0. In the rough scan processing, the position of the vessel 310, that is, the observation target range R0, may be acquired by, for example, image processing. FIG. 19 illustrates an example of vessel position acquisition based on image information on a plurality of acquired images. As shown in FIG. 19, the first control section 110 divides an observable range R of the observation apparatus 100 into a plurality of areas, and acquires an image signal for each of the divided areas. At this time, the first control section 110 also acquires position information on the position where the image is taken. The first control section 110 synthesizes images taken in each of the areas and produces a synthetic image. The first control section 110 acquires an observation target range R0 based on an analysis of the synthetic image and position information at the time of imaging. The observation target range R0 thus acquired is used in the scan processing or the like, as described above. FIG. 19 is a schematic view only for the purpose of explanation; the manner of division of the observable range R and the number of divided area are not limited to the example of this view.

In the example described above, the vessel position is determined on the basis of the acquired image information. The vessel position may be determined on the basis of the image information either by the first control section 110 or the user. For example, the user may determine the vessel position while observing the respective image data or synthetic image data of the divided areas included in the observable range R acquired as described above. The vessel 310 may be processed so that the vessel edge portion can be easily detected by image processing; for example, a reflective material, a distinctive structure, or the like may be added to the vessel edge portion.

(Second Modification Relating to Acquisition of a Vessel Position)

Alternatively, the vessel position may be acquired by a dedicated sensor. FIG. 20 illustrates an example of vessel position acquisition based on sensor output information. For example, as in the case of a configuration example shown in FIG. 20, the transparent plate 102 of the observation apparatus 100 includes a pressure sensor S1 in an area including at least the observable range R. The first control section 110 acquires an output signal from the pressure sensor S1, and acquires information, such as a vessel shape and a position where the vessel 310 is placed. In the example shown in FIG. 20, the pressure sensor S1 and the transparent plate 102 have the same length at one end of the area; however, the length is not limited to this example. Furthermore, the sensor is not limited to the pressure sensor S1. For example, the sensor may be a capacitance-type sensor or a brightness sensor.

The acquisition of the vessel position or the observation target range R0 is not limited to that of the embodiments and two modifications described above; the vessel position or the observation target range R0 may be acquired by an input by the user. For example, the user may set the vessel position or the observation target range R0 by inputting the coordinates thereof. Furthermore, as in the case of the first modification relating to acquisition of a vessel position, rough scan processing may be carried out before scan processing, and the user may input and set the vessel position or the observation target range R0 while observing an image obtained by the rough scanning.

(Modification Relating to a Vessel Type)

Figure 21A:
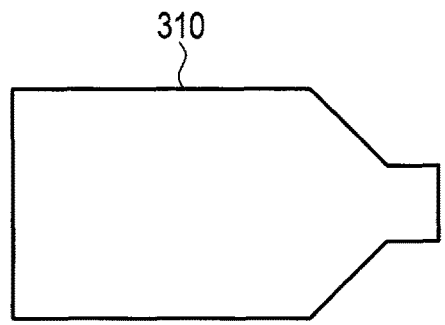
FIG. 21A is a view illustrating another example of a transparent vessel shape.
Figure 21B:
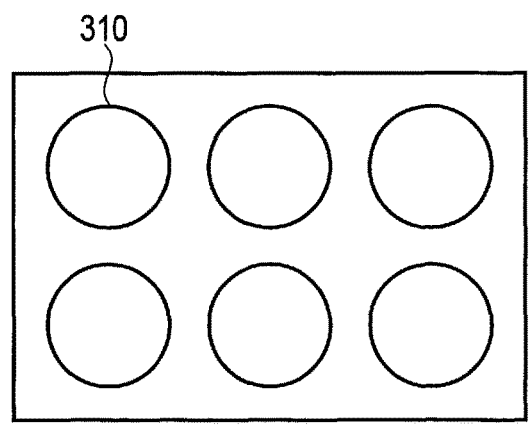
FIG. 21B is a view illustrating another example of a transparent vessel shape.

The examples of using the vessel 310, which is circular (for example, a petri dish), are described above, but the shape of the vessel 310 is not limited to the above. Other examples of the transparent vessel shape are shown in FIG. 21A and FIG. 21B. As shown in FIG. 21A, the vessel 310 may have a rectangular observation target range R0 as typified by a culture flask. Alternatively, as shown in FIG. 21B, the vessel 310 have an observation target range R0 as a part of a culture vessel formed of a plurality of culture areas as typified by a multi-well plate (multi-well dish). In each of the vessel types, position information on the observation target range R0 or the like is specified in advance and pre-stored in the first storage section 130 or the second storage section 230.

Furthermore, in the embodiments described above, the vessel 310 of the sample 300 is a transparent vessel including a part that is transparent to illumination light, and an object to be observed is placed in the transparent vessel. However, this is not restrictive. For example, depending on the object to be observed, even if a transparent vessel is not used, the first control section 110 can acquire the position of an edge portion of the object to be observed based on scattering of illumination light by the object itself to perform illumination control. The object to be observed is not limited to a cell. For example, the technique of the embodiments can also be applied to inspection of a material surface, if the object to be observed scatters or reflects illumination light.

(Modification Relating to a Configuration of the Measurement System 1)

In connection with the above embodiments, reference is made to the case where the observation apparatus 100 processes the images obtained by the imaging section 170 and analyses the measurement results. However, this is not restrictive. The second control section 210 of the controller 200 may perform at least one of these processes if unprocessed data is transmitted from the observation apparatus 100 to the controller 200. In other words, an apparatus, as one aspect of the present invention, can be modified in a number of ways. For example, it may be designed to cooperate with a number of apparatuses to attain the above-mentioned functions.

In the above embodiments, reference is made to the case where the transparent plate 102 covers the top of the casing 101 of the observation apparatus 100, and the sample 300 is placed on top of the casing 101. However, this is not restrictive. Depending upon the size of the object to be observed and the shape of the casing, the transparent plate need not be employed. The casing may just be a hollow member. The shape of the observation apparatus 100 may be properly varied in accordance with the form of the sample 300, the observation direction, or the like.

A change of the order of the processing or the steps in each processing illustrated by the flowcharts is possible. Addition or deletion of a processing or a step is also possible. The processing is executed by the corresponding programs stored in the first storage section 130 or the second storage section 230. Each of the programs may be stored in advance in the measurement system 1 or may be stored in another storage medium. The programs may be stored in various ways in the measurement system 1 or another storage medium; they may be stored before shipment, may be stored in a distributed storage medium, or may be stored through a communication line, such as the Internet.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An observation apparatus comprising:
an imaging unit comprising:
an imaging section that includes an imaging optical system and an image sensor and that images a sample to output an image signal; and
an illumination section that includes a plurality of emitting sections which are configured to emit illumination light and are located away from an optical axis of the imaging optical system and that illuminates the sample;
a driving mechanism that moves the imaging unit; and
at least one control circuit which
acquires position information on the imaging unit,
acquires position information on the sample,
selects which of the emitting sections emits illumination light based on the position information on the sample and the position information on the imaging unit,
causes the selected emitting section to emit main illumination light, and
causes the imaging section to perform imaging.

2. The observation apparatus according to claim 1, wherein the control circuit selects the emitting section that is nearer to a central portion of the sample from the emitting sections.

3. The observation apparatus according to claim 1, wherein the control circuit selects the emitting section further based on histories of lighting the emitting sections.

4. The observation apparatus according to claim 1, wherein the control circuit selects the emitting section further based on accumulated lighting time periods of the emitting sections.

5. The observation apparatus according to claim 1, wherein the control circuit acquires the position information on the sample based on the image signal output from the imaging section.

6. The observation apparatus according to claim 1, further comprising a sensor that is configured to detect a position of the sample, wherein the control circuit acquires the position information on the sample based on an output from the sensor.

7. The observation apparatus according to claim 1, wherein the control circuit divides a scanning range of the imaging unit into a plurality of areas based on the position information on the sample, and selects an emitting section that emits illumination light from the emitting sections based on which of the areas the imaging unit is in.

8. A method for controlling an observation apparatus that comprises: an imaging unit comprising an imaging section that includes an imaging optical system and an image sensor and that images a sample to output an image signal, and comprising an illumination section that includes a plurality of emitting sections which are configured to emit illumination light and are located away from an optical axis of the imaging optical system and that illuminates the sample; and a driving mechanism that moves the imaging unit, the method comprising:
- causing the driving mechanism to move the imaging unit;
- acquiring position information on the imaging unit;
- acquiring position information on the sample;
- selecting which of the emitting sections emits illumination light based on the position information on the sample and the position information on the imaging unit;
- causing the selected emitting section to emit main illumination light; and
- causing the imaging section to perform imaging.

9. The method for controlling an observation apparatus according to claim 8, wherein the selecting includes selecting the emitting section that is nearer to a central portion of the sample from the emitting sections.

10. The method for controlling an observation apparatus according to claim 8, wherein the selecting includes selecting the emitting section based on histories of lighting the emitting sections.

11. The method for controlling an observation apparatus according to claim 8, wherein the selecting includes selecting the emitting section based on accumulated lighting time periods of the emitting sections.

12. The method for controlling an observation apparatus according to claim 8, wherein the acquiring position information on the sample includes acquiring the position information on the sample based on the image signal output from the imaging section.

13. The method for controlling an observation apparatus according to claim 8, wherein the acquiring position information on the sample includes acquiring the position information on the sample based on an output from a sensor that is configured to detect the position of the sample.

14. The method for controlling an observation apparatus according to claim 8, further comprising dividing a scanning range of the imaging unit into a plurality of areas based on the position information on the sample, wherein the selecting includes selecting an emitting section that emits illumination light from the emitting sections based on which of the areas the imaging unit is in.

15. A non-transitory computer readable storage medium storing a control program for an observation apparatus that comprises: an imaging unit comprising an imaging section that includes an imaging optical system and an image sensor and that images a sample to output an image signal, and comprising an illumination section that includes a plurality of emitting sections which are configured to emit illumination light and are located away from an optical axis of the imaging optical system and that illuminates the sample; and a driving mechanism that moves the imaging unit, wherein the control program causes a computer to execute:
- causing the driving mechanism to move the imaging unit;
- acquiring position information on the imaging unit;
- acquiring position information on the sample;
- selecting which of the emitting sections emits illumination light based on the position information on the sample and the position information on the imaging unit;
- causing the selected emitting section to emit main illumination light; and
- causing the imaging section to perform imaging.

16. The non-transitory computer readable storage medium storing a control program for an observation apparatus according to claim 15, wherein
the selecting includes selecting the emitting section that is nearer to a central portion of the sample from the emitting sections.

17. The non-transitory computer readable storage medium storing a control program for an observation apparatus according to claim 15, wherein the selecting includes selecting the emitting section based on histories of lighting the emitting sections.

18. The non-transitory computer readable storage medium storing a control program for an observation apparatus according to claim 15, wherein the selecting includes selecting the emitting section based on accumulated lighting time periods of the emitting sections.

19. The non-transitory computer readable storage medium storing a control program for an observation apparatus according to claim 15, wherein the acquiring position information on the sample includes acquiring the position information on the sample based on the image signal output from the imaging section.

20. The non-transitory computer readable storage medium storing a control program for an observation apparatus according to claim 15, wherein
the acquiring position information on the sample includes acquiring the position information on the sample based on an output from a sensor that is configured to detect the position of the sample.

* * * * *